United States Patent
Kahelin et al.

(10) Patent No.: US 8,900,832 B2
(45) Date of Patent: Dec. 2, 2014

(54) METHOD FOR THE PRODUCTION OF FAT

(75) Inventors: Heidi Kahelin, Espoo (FI); Simo Laakso, Turku (FI); Ossi Pastinen, Kantvik (FI); Miia Mujunen, Helsinki (FI); Tarja Suomalainen, Helsinki (FI)

(73) Assignee: Neste Oil Oyj, Espoo (FI)

( * ) Notice: Subject to any disclaimer, the term of this patent is extended or adjusted under 35 U.S.C. 154(b) by 588 days.

(21) Appl. No.: 12/803,350

(22) Filed: Jun. 24, 2010

(65) Prior Publication Data

US 2011/0065940 A1 Mar. 17, 2011

Related U.S. Application Data

(60) Provisional application No. 61/269,426, filed on Jun. 24, 2009.

(30) Foreign Application Priority Data

Jun. 24, 2009 (FI) .................................. FI20095709

(51) Int. Cl.
*C12M 1/00* (2006.01)
(52) U.S. Cl.
USPC ............ 435/134; 435/261; 435/171; 435/162
(58) Field of Classification Search
None
See application file for complete search history.

(56) References Cited

U.S. PATENT DOCUMENTS

| | | |
|---|---|---|
| 2008/0160583 A1 | 7/2008 | Oyler |
| 2008/0160593 A1 | 7/2008 | Oyler |
| 2008/0175953 A1 | 7/2008 | Barcklay |
| 2009/0081742 A1 | 3/2009 | Dunlop et al. |
| 2009/0253169 A1 * | 10/2009 | Mayfield et al. ............. 435/69.1 |

FOREIGN PATENT DOCUMENTS

| | | |
|---|---|---|
| WO | WO2007/025145 | 3/2007 |
| WO | WO 2007/118223 A2 | 10/2007 |
| WO | WO2008/070281 | 6/2008 |
| WO | WO2008/151149 | 12/2008 |
| WO | WO2009/035551 | 3/2009 |
| WO | WO2009/063138 | 5/2009 |
| WO | WO 2009/086307 A1 | 7/2009 |
| WO | WO2009/149027 | 12/2009 |

OTHER PUBLICATIONS de Vries and Visser, "*Aspergillus* Enzymes Involved in Degradation of Plant Cell Wall Polysaccharides." (2001) Microbiology and Molecular Biology Reviews, 65(4), 497-522.*
Wang et al., "Fermentation and Enzyme Technology" (1979) Wiley, pp. 116-117.*
Chatzifragkou,A et al, Commercial Sugars as Substrates , Eur.J. Lipid Sci. Technol. 2010,112, 1048-1057.
Fakas,S, et al, Evaluating Renewable Carbon Sources as Substrates, Biomass and Bioenergy 33 (2009) 573-580.
Li Q, et al, Perspectives of Microbial Oils For Biodiesel Production, Appl Microbiol Biotechnol (2008) 80: 749-756.
Liu, B, et al, Biodiesel Production by Direct Methanolysis, J Chem Technol Biotechnol 82: 775-780 (2007).
Colin, R et al, Microbial and Algal Oils, Lipid Technology, Jul. 2008, vol. 20, No. 7, 155.
Vamvakaki, A, et al, Cheese Whey as a Renewable Substrate For Biomass Production, Eng. Life Sci. 2010, 10, No. 4 348-360.
Vicente,G, et al Biodiesel Production From Biomass of an Oleaginous Fungus, Biochemical Engineering Journal 48 (2009) 22-27.
Dahui,X, et al Biomass Carbohydrates Assimilation and Lipid Accumulation , ISSN 1000-3061, vol. 26 No. 2 189-193, Feb. 2010 abstract only.

* cited by examiner

*Primary Examiner* — Jon P Weber
*Assistant Examiner* — Teresa E Knight
(74) *Attorney, Agent, or Firm* — Andrus Intellectual Property Law, LLP

(57) ABSTRACT

The present invention relates to a method for the production of fat with a principal application as transportation biofuel or a component or raw material therefor. According to the method, cell masses, cell suspensions and/or liquid phases formed in the production of single cell oil, and/or biomass-containing side streams or microorganism cell masses for another purpose and/or originating from other sources, are contacted with a fat-production capable microorganism and the organism is allowed to produce fat. The resulting fat is recovered or the microorganism mass is passed to a single-cell oil production process. By means of the invention, the organic matter present in the cell mass and side streams of single-cell oil can be re-utilized for the production of the single-cell oil, thereby improving a total fat yield, as well as reducing an organic load of the side streams.

7 Claims, 6 Drawing Sheets

METHOD FOR THE PRODUCTION OF FAT

PRIORITY

This application claims priority of the U.S. provisional application No. 61/269,426 filed on Jun. 24, 2009 and of Finnish national patent application number 20095709 filed Jun. 24, 2009.

FIELD OF THE INVENTION

The present invention relates to a method for the production of fat. Specifically, the invention relates to the use of side streams obtainable from a single-cell oil production process or the use of an obtained cell suspension or cell mass for the production of fat. The method according to the invention provides an improvement for the total fat yield of a single-cell oil production process.

BACKGROUND OF THE INVENTION

Environmental and climate issues, as well as a concern about the sufficiency of fossil energy sources, have brought up a need for alternative energy sources. Renewable biomaterials represent a sustainable natural resource, but the utilization thereof as a substituent for fossil energy sources presents all in all one of the most extensive challenges for the future society from the standpoint of technology, economy, and ecology. The production of transportation fossil fuels alone is immensely large-scale business, and even a partial replacement of this production with biofuels calls for a significant technological leap in order to make the processing of biomaterials viable in large-scale industrial production. Indeed, a leading thought in this technological development is to work out the way of utilizing comprehensively and effectively the limited biomass and its various forms as components applicable to the manufacture of biofuel.

The natural processing of a biomaterial into biofuel could be ideally based on a microbiological process, wherein a biomass with a relatively low average energy content is used for producing components suitable for the manufacture of biofuel. A biotechnological mode of production that has been proposed in literature is the microbiological production of single-cell oil.

Based on generally known literature, the production of single-cell oil can be regarded as including steps of producing single-cell organisms, allowing the cells to produce oil, extracting and recovering the oil (Ratledge et al., 2005, Ratledge and Hopkins, 2006, Ratledge and Wilkinson, 1988 and 1989, Meng et al., 2009).

One of the proposed applications for single-cell oil has been its use as a special oil, in reference to health functionality or nutritional aspects. In this type of single-cell production processes, with moderate output rates, the biomaterials used as a feedstock, the individual operations, and costs incurred thereby, do not constitute an essential commercial obstacle in view of the expected value of the product.

Methods involving essentially the same process steps have also been described in reference to producing single-cell oil for use as components of biofuel. (Ratledge and Cohen 2008). In these processes, the recovered oil is processed for an alcohol ester of fatty acids, especially for methyl ester.

Hence, the basic technology for producing single-cell oil (subsequently "single-cell fat") is known. However, the prior known technology does not provide adequate preconditions neither for commercially viable nor ecologically sustainable biofuel process (Ratledge and Cohen 2008). This is revealed even by a rough examination of carbon balance. As for the biomass feedstock used for a single-cell production process, about a third is released as carbon dioxide and about 40-80% of the remaining biomass consists of residual biomass after the extraction of oil. Based on a theoretical study alone, it can be noticed that, regarding the carbon contained in biomass used as a feedstock, the maximum recovery in the form of fat is about 30%. In practice, the carbon balance will be even remarkably lower than that, e.g. for the reason that the large amount of process water required by a microbiological process shall retain plenty of feedstock-based organic matter in a dilute and therefore hard-to-exploit form.

From the aspect of energy balance, as well, the prior art single-cell fat process is quite problematic. A still unanswered question is how the biomass, consisting of cell residues after the removal of oil, could be processed energy efficiently and how the organic carbon matter, present in the process water in a dissolved or dispersed dilute form, could be reclaimed and processed in energy efficient ways.

A solution for the poor overall use of biomass in the biotechnological manufacture of transportation fuel has been proposed in patent publication WO 2008134836. The solution described in the cited patent publication relates to the production of fat from a side fraction obtained in the treatment of sugar cane to make it suitable for the manufacture of ethanol. The discussed side fraction is used for cultivating autotrophic algae and fat-accumulating yeast.

With regard to this problem area, it has been proposed in patent publications WO 2009046375 and US 20090064567 A1 that spent nutrient solution residues and cell residues be treated in a way of making the same useful as a nutrient for microorganisms for providing polyunsaturated fatty acids or for implementing the production of methyl esters of ethanol or fatty acids. According to the cited publications, the discussed side streams call for diverse treatments, undermining the viability of using large side stream amounts.

The use of prior known single-cell fat production processes, according to the prior art, is not economically sensible, nor is it consistent with sustainable development to use such processes, especially for the large-scale manufacture of transportation fuel.

SUMMARY

The present invention pursues to provide a solution to problems encountered as current technology is used in the production of single-cell fat. Specifically, the present invention pursues to provide a technically beneficial solution to problems encountered in the large-scale production of single-cell fat.

In order to achieve this object, the invention is characterized by features set forth in the independent claims. Other claims present some preferred embodiments of the invention.

Another object of the present invention is to provide a solution, which enables upgrading the economy of large-scale single-cell fat production and reducing the environmental burden.

The present invention pursues particularly to work out problems related to the manufacture of transportation biofuel.

The method according to the invention is based on the aspect that cell masses, cell suspensions formed from single-cell fat production and/or side streams associated with the formation thereof and/or side streams or microorganism cell masses originating from other sources will be reutilized for producing single-cell fat, thereby reducing an organic load of the side streams.

In single-cell fat processes of the prior art, the manufacture of fat is implemented by means of microorganisms, such as yeast and algae. The production process yields cell mass and side streams, which still contain a fair amount of organic matter. The present invention is based on having single-cell production processes accompanied by new microbiological processes, by means of which the organic matter present in cell mass and side streams can be utilized and fat can be produced. This enables improving the single-cell oil production process in terms of its total fat yield, mass balance and/or energy balance.

Fat production can be effected by using microorganisms, such as algae, yeasts, and molds, capable of producing fat. It is particularly preferred to utilize the ability of molds (filamentous fungi) to produce fat.

According to one preferred embodiment of the invention, by way of utilizing side stream biomasses, formed in a single-cell fat production process and being partially or totally free of single-cell fat, there is produced by means of microorganism cultures, a single-cell fat and a total fat yield is thereby enhanced.

According to a second preferred embodiment of the invention, by way of utilizing cell suspensions or cell masses derived from a single-cell fat production process, there is produced, by means of microorganism cultures, a single-cell fat and a total fat yield is thereby enhanced.

According to a preferred embodiment of the invention, the single-cell mass, formed as a side stream in a single-cell fat production process, is employed, as such or fractionated to various degrees, as a starting material for the production of single-cell fat, as such or admixed with other side streams or liquid media.

According to yet another preferred embodiment of the invention, the cell-free or almost cell-free liquid side stream, releasing from a single-cell fat production process, is used as a starting material for the production of single-cell fat, as such, concentrated, diluted or admixed with other side streams or liquid media.

According to a further preferred embodiment of the invention, the side stream, containing a cell mass, formed as a side stream in a single-cell production process, cells, cell residues or a cell-free or almost cell-free liquid side stream, is used in various mixtures for the production of single-cell fat.

Further, according to some preferred embodiments of the invention, the production of single-cell fat is effected by using fractions of a cell suspension derived from a production process of the above-mentioned single-cell fat, or fractions of a residual cell mass, a liquid phase or mixtures thereof obtained by extracting therefrom.

The term "side stream" is also used in this description in reference to cell masses and cell suspensions in a single-cell fat process.

The reutilization of biomass-containing side streams obtained from a single-cell fat production process can be effected in such a way that these new microbiological processes are combined with the single-cell production process functionally or in such a way that processes take place separately.

According to preferred embodiments of the invention, the single-cell fat, obtained by means of side streams reutilized in microbiological processes, is conducted to a known single-cell fat process for the recovery of fat.

If necessary, the most preferred embodiment for a method of the invention can be selected and defined according to the side stream which has the best cost efficiency in terms of carbon and energy balance from the standpoint of exploiting the side streams.

The cultivation medium used for the cultivation of microorganisms and the production of single-cell fat can also be supplemented with streams other than those mentioned above forming in single-cell fat production and containing organic matter.

According to one preferred embodiment, the cultivation medium is further supplemented with nutrients. The purpose of these is to improve the growth and/or the fat producing capacity of microorganisms used in the production of single-cell fat.

According to yet another preferred embodiment of the invention, the side streams developing in a single-cell fat production process are treated chemically or microbiologically. Such a treatment can be incorporated in a desired process step in the single-cell fat production process. The purpose of treatments is to improve the side streams obtained in a single-cell fat production process in terms of their usefulness in the production of single-cell fat.

According to one preferred embodiment of the invention, it is beneficial that a fat production process, which is based on microorganisms capable of the production of fat, be combined with cell suspensions obtained from single-cell fat production or other sources.

According to the invention, the carbon dioxide, developed in a single-cell fat process based on the treatment of side streams and making use of hetero- or mixotrophic microorganisms, can be conducted to the cultivation of an autotrophic or mixotrophic organism, such as algae or cyanobacteria.

According to a preferred embodiment of the invention, the single-cell fat, manufactured according to the present description, can be used particularly for the manufacture of a transportation fuel made from renewable raw materials.

The prior art publications do not reveal a solution as to how the processes, based on the side streams of microorganism cultures, could be linked with processes producing side streams in such a way that these processes would jointly lead to an improvement of the total fat yield and the energy and mass balances of the process. Neither has the prior art shown any technology for using the side streams of a single-cell fat process in themselves for the production of single-cell fat. Nor is there any suggestion in the prior art to the effect that the fat, produced by a combined solution of producing side streams and utilizing the same, could be used for the manufacture of a renewable transportation fuel.

The method according to the invention resolves the problem of how a poor carbon and energy balance of the carbon in a biomass fed into a single-cell fat production process can be improved in a large-scale industrial process. By means of the invention, the side streams, resulting from the production of single-cell fat, can be further used for making single-cell fat and thereby for reducing the loss of organic material caused by the side streams of single-cell fat production and the burden cost incurred by a further treatment of this material. Benefits of the invention emerge as obvious when considered in proportion to the present and ever increasing global scale of the production and use of transportation fuels. The invention enables upgrading the utilization rate of organic biomass needed for the manufacture of transportation biofuel (e.g. biodiesel or a renewable transportation fuel), and thereby improving the sufficiency of its supply.

It is a particular benefit of the invention that a microbiological process can be supplied with an organic material stream derived from several diverse sources, either as such or combined with the streams of single-cell fat production processes.

The invention enables carrying out the method by means of single-cell fat production processes based on a number of various microorganisms. A particularly advantageous approach is to link single-cell fat production processes with single-cell fat production based on molds (filamentous fungi).

The invention enables replacing entirely or partially the recycling of residual biomass produced in single-cell fat production by using chemical hydrolysis methods based on acid and/or alkaline catalysts, thus avoiding the formation of salt accumulating in liquid phases of processing.

The method according to the invention is simple and very modest in its energy demand.

The invention can be implemented by using verifiably safe and industrially applicable microorganism species.

The method according to the invention lends itself to implementation in keeping with several different embodiments. A common feature for the embodiments is their performance of improving carbon and energy balances over the prior art while reducing an organic load caused by the side streams of single-cell fat production processes.

The invention introduces a substituting solution for the chemical treatment of side stream biomasses, the purpose of such treatments being either to reduce an environmental burden created by the side streams or to produce from the side stream biomasses a reusable nutrient for single-cell fat producing microorganisms.

Side stream biomasses can be subjected to chemical treatments, such as acid and alkali treatments, as well as to enzyme treatments or combinations thereof for converting carbohydrate and protein mass into oligo and monomeric forms used by single-cell fat producing microorganisms. However, these hydrolysis treatments may be relatively incomplete as a result of the chemical and physical makeup of the surface compositions of a cell material, which jointly provide an effective resistance to acid and alkaline catalytic hydrolyses. Therefore, the chemical hydrolyses occurring in the polymer structures of the organic coat layers of single-cell organisms are typically incomplete. In addition to this, the carbohydrate monomers and nitrogen compounds created as side reactions of chemical hydrolyses endeavor to continue reacting with each other, resulting in compounds which are no longer suitable for use as carbon or nitrogen sources for fat-accumulating microorganisms, or said compounds may inhibit the growth of microorganisms. By means of the invention, these chemical treatments can either be replaced entirely or applied as a sub-stage in accordance with the invention.

The invention also provides a solution regarding the recycling of utilizable organic carbon compounds, contained in the process water resulting from single-cell fat production, back into the single-cell fat production process, as well as regarding the recycling of other nutrients present in the process water for the purpose of promoting the formation of single-cell fat. By means of the invention, a liquid side stream can be made cleaner by removing some of the nutrient and metabolic residues contained therein, thus reducing the ecological burden of the liquid side stream with a beneficial effect on the cost structure of a single-cell fat process.

Also, the methods according to the invention enable making use in microbial fat production of the nutrients of fat-containing cell suspensions obtained from a single-cell fat production process, or those contained in otherwise obtained cell masses, cell suspensions or liquid phases associated therewith.

The method according to the invention enables making use of the diverse genetic capabilities of various microorganisms for the utilization of nutrients and various carbon sources and for the production of fat.

The methods according to the invention provide for a new type of solution in terms of how to utilize renewable biomass for producing components of transportation biofuel in a way to combine a more comprehensive and thereby more conservative use of natural resources, environmental soundness, and improvement of commercial viability.

The invention contributes to the creation of conditions that enable the application of microbiological single-cell fat production to large-scale industrial oil production.

In summary, it can be concluded that the invention offers benefits in that
  the total fat yield of a single-cell fat production process improves,
  the carbon and energy balance of single-cell fat production processes improves,
  the environmental burden caused by single-cell fat production is reduced,
  costs incurred by side streams originating from single-cell fat production are reduced,
  the manufacturing efficiency of single-cell fat improves,
  the method is simple and very modest in its energy demand,
  the amount of recycled water is reduced,
  the method according to the invention can be implemented with verifiably safe and industrially applicable microorganism strains,
  the utilization rate and sufficient supply of organic biomass needed for the manufacture of transportation biofuel can be improved,
  the invention enables replacing totally or partially the recycling of residual biomass resulting from single-cell fat production by using chemical hydrolysis methods based on acid and/or alkaline catalysts, thus avoiding the formation of salt accumulating in the liquid phases of processing and/or the formation of compounds hindering the activity of microorganisms.

According to a preferred embodiment of the invention, a microbiological process, which makes use of the side streams of a single-cell fat process, can be integrated with the single-cell fat process. In this case, the single-cell fat process, which makes use of side stream biomass, does not require a separate fat-reclaiming unit process but, instead, the recovery of fat can be conducted in the same unit process used also for the fat recovery of a primary single-cell fat process.

BRIEF DESCRIPTION OF THE FIGURES

FIG. 1 shows a diagram for the use in mold cultivation and fat production of a supernatant and a residual cell mass extracted from a single-cell fat production process after the recovery of fat.

FIG. 2 shows the use of a supernatant and a residual cell mass, possibly supplemented with nutrients, in mold cultivation and fat production.

FIG. 3 shows the use in mold cultivation and fat production of a residual cell mass extracted after the recovery of fat and treated with chemical hydrolysis.

FIG. 4 shows the use in mold cultivation and fat production of a supernatant and a residual cell mass extracted after the recovery of fat, and the chemical hydrolysis and use of a thus obtained residual biomass in single-cell mass cultivation and fat production.

FIG. 5 shows the mold treatment and use of a residual cell mass in mold cultivation and fat production sequentially and simultaneously (mixed culture).

FIG. 6 shows the use of a supernatant and a residual cell mass in mold cultivation and fat production supplemented with nutrients.

FIG. 7 shows a diagram for the use of a cell suspension, possibly supplemented with nutrients, in mold cultivation and fat production.

DETAILED DESCRIPTION OF THE INVENTION

Figure 1:
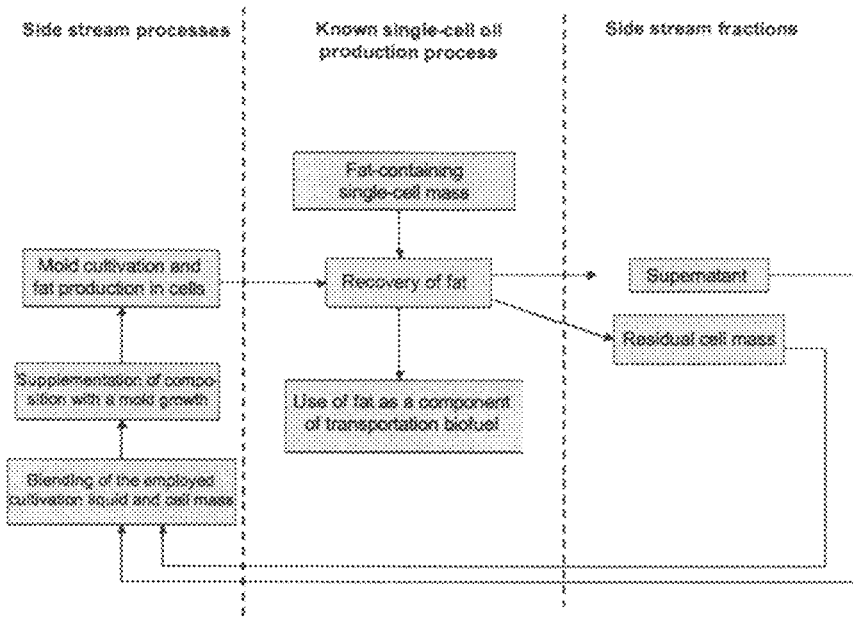
FIGS. 1-7 show preferred embodiments of the invention in diagrams.

The present invention is based on experimental observations about microbiological single-cell fat production processes consistent with the current state of the art:

In the process of recovering fat produced by means of microorganisms, the cells must typically be disintegrated and the fat extracted. However, regardless of which cell disintegration method is used, just some of the cells containing single-cell fat are broken up.

After the extraction of fat, the cell mass shall typically still retain 2-25% of fat.

The cultivation solution or supernatant, remaining after the cell extraction from the cultivation of cells and the fat production step, contains organic carbon compounds.

The supernatant and the cell mass after cell extraction comprise jointly a share of 20-60% of the carbon used as a carbon source.

A surprising discovery in the present invention was that

The microorganism capable of fat production was using a cell-free growth solution, released from state-of-the-art single-cell fat production, for its growth and for the production of a microorganism-based single-cell fat.

The single-cell fat producing microorganisms were also using disintegrated single-cell cellular residues for growth and fat production.

In addition to this, the discussed microorganisms were also using intact yeast and algal cells for their growth and fat production.

Effective microbial growth and fat production were achieved both in the supernatant, in a supernatant supplemented with a carbon source and in mixtures composed by a growth solution and intact or broken cells.

The above-described surprising discoveries formed a foundation for the invention to combine a fat production process, based on microorganisms capable of producing fat, with side streams of a primary single-cell production process, and to thereby improve the overall fat yield, mass balance and/or energy balance of the process.

It was further found beneficial to combine a fat production process, based on microorganisms capable of producing fat, with cell suspensions obtainable from a known single-cell fat production process or some other source, with cell masses or with liquid phases obtained from these processes.

It is also advantageous to combine a microbiological process, utilizing side streams of a known single-cell fat process, with the single-cell fat process. In this case, both processes may use for example a common fat recovery process in the single-cell fat process.

DEFINITIONS

Fat stands for a lipid, oil, fatty substance, generally having a molecular moiety in the form of an aliphatic hydrocarbon chain soluble in organic solvents, but poorly soluble or insoluble in water. In the present invention, the fat is intended to principally comprise tri-, di- or monacylglycerols or sterol esters, but cells can also develop other fats, such as phospholipids, free fatty acids, sterols, polyprenols, sphingolipids, glycolipids, and diphosphatidylglycerol.

Fat-producing microorganisms stand for microorganisms, whose metabolism proceeds to the production of storage fats in nutrient-limited, typically nitrogen-limited growth conditions with some carbon source still available, as opposed to low fat-producing microorganisms, which store energy in the form of other storage polymers, such as starch. Typically, the fat-producing microorganisms have an ATP:citrate-lyase enzyme, therefore having an ability to store fat in their cells, said fat being mainly triacylglycerol or triglyceride. The fat-producing microorganisms are typically algae, yeasts or molds.

Mold treatment refers to a treatment in conditions which enable the growth of mold and/or the buildup of intracellular fat in mold.

Single-cell fat production process refers to the treatment of a fat-producing microorganism with techniques known to a skilled artisan and described in literature for the production of cell mass and intra-cell fat.

Known single-cell fat production process, i.e. in this context "the first or primary stage single-cell fat production process", stands for a process, comprising steps of forming or allowing the formation of a fat-synthesizing microorganism and allowing the thus obtained organism mass to produce and store fat, extracting and recovering the cells from the liquid phase, and extracting the fat from the cells.

Methods presented in this description can be accompanied with the known single-cell fat production process, but also with single-cell fat production processes to be developed later.

Fat recovery refers to a process, in which the intra-cell fat is recovered by mechanical, chemical, thermomechanical or autocatalytic methods or by a combination of these methods.

Cell suspension obtainable from single-cell fat production process refers to a cell suspension developed in the production of single-cell fat, particularly to such a cell suspension, which has not yet been subjected to the extraction of fat.

Cell suspensions obtainable from other microbiological processes refer, for example, to yeast cells used in the production of ethanol, or to cell suspensions obtainable from other sources, such as algal growths, for example aquatic algae, including cyanobacteria, or microorganism masses from biotechnological production processes.

Single-cell fat stands for an intra-cell fat that has been intracellularly synthesized by microorganisms, a fat excreted by the cell, as well as a fat present in the structural parts of a cell, such as in membrane systems.

Residual cell mass stands for a solid, semi-solid or flowing material fraction, which contains microorganisms treated for the recovery of intracellular fat.

Cell mass obtainable from other microbiological processes refers, for example, to yeast cells used in the production of ethanol, or cell masses obtainable from other sources, such as algal growths, for example aquatic algae, including cyanobacteria, or microorganism masses from biotechnological production processes.

Supernatant stands for a substantially cell-free substance fraction, which consists of a microorganism growth as a result of the extraction of cells. Another applicable expression for supernatant is a liquid phase.

Fat-containing single-cell mass stands for an autotrophically, heterotrophically and/or mixotrophically formed single-cell mass and cellular mycelium with a fat content of 10% or more of dry matter.

Methods according to this invention can be used not only for the treatment of side streams, a cell suspension or a cell mass obtainable from a single-cell fat production process, but also for the treatment of fat-containing industrial, community, household waste and/or an agricultural product or by-product.

Nutrients supplemented in a microorganism cultivation medium refer to compounds and components enabling the growth of a microorganism and/or the production of fat or promoting growth and fat production. These include typically various sources of carbon, nitrogen and phosphorus, inorganic salts and trace elements. The cultivation medium can be supplemented with natural or man-made fractions, which contain carbohydrates, preferably carbohydrate polymers containing hexose sugar, pentose sugar, either one or both of these, or fractions, which contain cellulose, starch, non-starch polysaccharide or lignocellulose. The supplementation of nutrients in the cultivation medium is not absolutely necessary, but may be advisable in certain cases.

Enzymes hydrolyzing cell walls refer typically to enzymes capable of hydrolyzing carbohydrate polymers, such as cellulase, hemicellulase, glucanase, lysozyme, cutinase, phytase or amylolytic enzymes.

Inducibility of enzymes refers to the fact that enzyme is only synthesized by the activity of an enzyme substrate or other compound acting as an inducer or an external factor. The present invention comprises utilizing the inducibility of enzymes, such that the enzymes, which disintegrate cell structures and/or hydrolyze components of the cell structures, are allowed to become synthesized only when it is desirable to use such enzymes for the disintegration of cells.

Microorganisms capable of producing fat are grown in cultivation conditions suitable for the production of lipids. The cultivation conditions suitable for the production of lipids refer to conditions in which the formation and accumulation of fat takes place in response to the composition of a cultivation medium, an external factor or both.

Biodiesel stands for diesel-grade methyl ester useful as biodiesel, as set forth in EU directive 2003/30EC, which has been produced from oil of plant or animal origin ("biodiesel" means a methyl-ester produced from vegetable oil, of diesel quality to be used as biofuel"). In addition, biodiesel can be manufactured of fat derived from microorganisms, such as yeast, mold or algae.

According to a preferred embodiment of the invention, the single-cell fat manufactured as presented in the present description is particularly applicable for producing transportation fuel made from renewable raw materials. The manufacture of renewable transportation fuel has been described in patent publications EP 1 396 531, EP 1 398 364, EP 1 741 767 and EP 1 741 768.

"Renewable transportation fuel" or "transportation fuel manufactured from renewable raw materials" refers to a fuel, which is manufactured by using a hydrogen treatment from animal, plant or microbial lipids or a blend thereof, when the microbial lipid can be derived from yeast, mold or algae. Optional procedures include isomerization or other process alternatives in addition to hydrogen treatment.

In contrast with the manufacture of biodiesel (methyl ester of fatty acids), it is typically preferred to use saturated fatty acids in the manufacture of renewable transportation fuel (a paraffin-based fuel produced by hydrogen treatment).

In the present invention, "suitable for renewable transportation fuel and/or biodiesel production" may preferably refer to a pretreated fraction suitable both for the production of biodiesel and for renewable transportation fuel production, especially to a lipid suitable for the production of a renewable transportation fuel and cleaned of impurities.

Carbohydrates stand for organic molecules, incorporating an aldehyde, acid or keto group and, in addition to these, several hydroxyl groups. Thus, the range of hydrocarbons encompasses compounds described by terms such as monosaccharide, oligosaccharide, sugar, cellulose, hemicelluloses, starch and non-starch hydrocarbon.

Cellulose is a long-chain polysaccharide, having a primary structure which consists of polymer created by β-1-4 glucose bonds.

Starch is a long-chain polysaccharide, consisting principally of α-1-4 and α-1-6 glucose units.

Monosaccharide is a monomeric unit of carbohydrates, $(C—H_2O)_n$, which typically consists of 3-9 carbon atoms and which has stereochemical inconsistencies in one or more carbon atoms. These are represented by hexoses, such as glucose, galactose, mannose, fructose, which have 6 carbon atoms, and pentoses, such as xylose, ribose and arabinose, which have 5 carbon atoms.

Pentose sugar stands for a monosaccharide containing five carbon atoms.

Hexose sugar stands for a monosaccharide containing six carbon atoms.

Hydrolysis or chemical hydrolysis refers to the cleavage of a carbon-carbon, carbon-oxygen, carbon-nitrogen, or carbon-sulphur, carbon-phosphorus bond either by the activity of water, acid or alkali, irrespective of the participation of water in the reaction. In enzymatic hydrolysis, the respective reactions take place in response to being catalyzed by enzymes. An example of hydrolysis is a reaction, in which an O-glycosidic bond between the monosaccharides of carbohydrates or a peptide bond between the amino acids of proteins is broken up.

Water, acid or alkaline treatment refers in this context to a process, in which an organic material, either as such or a product derived therefrom, is extracted, treated mechanically, thermomechanically, or is subjected to combinations of these treatments in the presence of water, acid or alkali.

Microorganism capable of fat production refers in this specification to a microorganism, such as yeast, algae or mold, preferably mold, capable of producing fat. The microorganism capable of fat production is in this description used for the utilization of the side streams, a cell suspension or cell mass of single-cell fat processes, or fractions from other sources, containing liquid phases or nutrients involved in the formation thereof, or cell mass from other sources. In one embodiment the microorganism may, in addition to fat production, be capable of producing enzymes disrupting cell structures and/or hydrolyzing ingredients of cell structures. In another embodiment a first microorganism may be capable of producing enzymes disrupting cell structures and/or hydrolyzing ingredients of cell structures, and a second microorganism may be capable of fat production.

First stage single-cell fat production process or primary single-cell fat production process refers to a prior known single-cell fat production process.

Second stage single-cell production process or secondary single-cell production process is a term used for a process, which utilizes side streams of a single-cell fat production process, cell suspension, cell mass, liquid phase, or cell masses, cell suspensions or liquid phases related thereto from other sources, or nutrient-containing streams from other sources, possible in combination with said cell suspensions, cell masses or liquid phases, in order to distinguish this process from the single-cell fat production process. The second stage fat production process results in the formation of "second stage single-cell fat" and "second stage single-cell mass", typically "mold fat" and "mold mass".

In some embodiments of the invention the starting material may comprise at least 20 wt-%, preferably at least 30 wt-%, preferably at least 40 wt-%, more preferably at least 50wt-%, more preferably at least 60 wt-%, still more preferably at least 70 wt-%, still more preferably at least 80wt-%, still more preferably at least 90 wt-% side streams or cell suspension of a single-cell fat production process. The rest of the starting material may comprise cell suspension, cell mass, or liquid phase related thereto from other sources, such as for example from other microbial process or from environment, such as cell mass from biotechnical process, yeast mass from ethanol production or algal mass from a body of water, or a biomass from other sources, such as for example industrial, community, household waste, and/or agricultural products or by-products (i.e. nutrient-containing streams from other sources). In some embodiments the starting material may comprise cell suspension, cell mass, liquid phase, or cell masses from other sources than single-cell fat production process less than 80 wt-%, less than 70 wt-%, less than 60 wt-%, less than 50 wt-%, in some embodiments less than 40 wt-%, less than 30 wt-%, in some embodiments less than 20 wt-%, less than 10 wt-%, or less than 5 wt-%. Correspondingly the amount of biomass from other sources may be less than 80 wt-%, less than 70 wt-%, less than 60 wt-%, less than 50 wt-%, less than 40 wt-%, less than 30 wt-%, less than 20 wt-%, less than 10 wt-%, or less than 5 wt-%.

Second stage single-cell mass and fat refer to a cell mass or fat produced by fat producing microorganisms, preferably molds, through the use of a material, a component or a compound originating from earlier processes, such as from the production of single-cell fat.

Side streams or side-stream fractions stand for any aqueous solutions or supernatants releasing from the production of cells, the production of single-cell fat, the recovery of cells or the extraction of fat, and for a post-fat extraction mixture of variably broken and intact cells, i.e. a residual cell mass or cell suspension or cell mass.

The term side stream or side-stream fraction is also used in reference to all fractions, containing an organic material and originating from sources other than single-cell fat production, and containing ingredients applicable for the growth of a microorganism, preferably mold, and for fat production, either as such or supplemented with other nutrient components.

According to preferred embodiments of the present invention, various microbiological single-cell fat production processes are linked functionally with each other, such that the carbon source, which has been fed into a single-cell fat production process of the prior art, typically based on yeasts and algae, can be applied to a more-than-before comprehensive use for the production of single-cell fat.

The invention enables the utilization of organic compounds releasing from a single-cell fat production process by enabling the reuse of post-fat extraction side streams as a cultivation medium or part of a cultivation medium for a single-cell fat producing microorganism, preferably mold, by using either all streams comprehensively, parts of these streams or combinations thereof.

The invention also enables the use of a fat-containing cell suspension, originating from a single-cell fat production process, as a cultivation medium or part of a cultivation medium for a single-cell fat producing microorganism, preferably mold, either in its entirety or in parts or in various combinations with post-fat extraction side streams originating from the single-cell fat production process.

Respectively, the invention also enables the use of cell suspensions, originating also from microorganism processes other than the single-cell fat production process, or nutrient-containing side streams, originating from other sources, as a cultivation medium or part of a cultivation medium for a single-cell fat producing microorganism.

Various processes can be interlinked functionally or can be implemented separately. The biomass-containing fractions obtained from a prior art single-cell fat production process, optionally with biomass-containing fractions obtained from other sources, can be transported to another process based on producing the fat of microorganisms and located for example in another region.

According to the invention, the recovery of fat (extraction of oil) of a primary and side-stream utilizing fat production process can be preferably implemented in one and the same unit process. Alternatively, the recovery of fat can be carried out in separate unit processes.

The method according to the invention is preferably based on the treatment of a cell suspension obtained from single-cell fat production or side-stream biomasses with microorganisms capable of single-cell fat production, such as molds, yeasts or algae. The invention is characterized in that the employed microorganisms are capable of growing and producing cell mass with side streams coming from single-cell fat production, either with these side streams as such, with combinations thereof, or by being supplemented with other nutrients. The invention is further characterized in that the discussed microorganisms are capable of producing single-cell fat by using as a starting material the side-stream biomasses of single-cell fat production processes based on yeasts, molds or microalgae or the biomass-containing fractions coming from other sources.

According to preferred embodiments of the invention, the above-mentioned cell suspensions or side streams can also be used just for the production of cell mass, and the second stage single-cell fat production can be implemented with components other than those originating from the side streams. Alternatively, the cell mass can be produced with components essentially other than those originating from side streams, and the side streams, in various forms thereof, are used for producing a second stage single-cell fat for the thus produced cell mass.

The invention encompasses also integrated microorganism processes, which employ the biomass side streams of a single-cell fat for growing themselves, or, respectively, microorganism processes, in which the dominating process is not the growth but, instead, the formation of single-cell fat.

The invention encompasses also processes, which make use of cell suspensions obtained from a single-cell fat production process and containing fat produced by the single-cell fat process.

The invention further comprises integrated microorganism processes, which are characterized in that the process comprises a first microorganism, for example a mold strain, which is capable of splitting polymeric organic compounds—such as cellulose, hemicelluloses, starch, non-starch carbohydrates, protein, and carbohydrates found in the surface structures of microorganism cells—and a second microorganism, such as a mold strain, which is capable of using the resulting hydrolysis products for its growth and single-cell fat production. Such processes can be implemented either as sequential processes or concurrently by using microorganism growths. A microorganism strain capable of splitting polymeric organic compounds can be replaced by using enzymes with a capability of splitting such compounds. The enzyme treatment can be conducted prior to or concurrently with the microorganism-effected production of single-cell fat.

The invention encompasses also processes, in which, in addition to the side streams of single-cell fat production covered by the invention, the microorganism cultivation medium comprises organic matter other than what results from single-cell fat production.

The method according to the invention, in preferred embodiments, includes steps, in which an intracellular fat accumulating microorganism, preferably mold, is grown on a cultivation medium, which is made of or which contains microorganism mass used for the production of single-cell fat, a fraction thereof, or a liquid phase left over from fermentation of the microorganism, a supernatant, or mixtures thereof in various degrees, and the microorganism, preferably mold, is allowed to produce fat, the fat is extracted by known techniques from the cultivation medium and the fat is used as biofuel or a raw material or component for biofuel or a raw material or component for foodstuffs or fodder.

The cultivation medium for a microorganism, preferably mold, capable of producing fat contains preferably microorganism mass, which has been used for the manufacture of a raw material or component of biofuel, or which originates from a microbiological biofuel manufacturing process or other single-cell mass, from which some of the fat component has possibly been extracted as described in the prior art. The microorganism mass contains preferably some cell ingredient originating from yeast, microalgae or molds, entire cells or a mixture thereof. These ingredients may also appear in admixtures with a liquid phase released from single-cell fat production or some other process. In an alternative embodiment of the invention, the cultivation medium may comprise the use of a single-cell fat production leftover solution, supernatant, as such, in a partially concentrated form, or having these fractions supplemented with nutrients capable of promoting the production of microorganism mass, such as mold mass or a fat of microorganism origin. Further, in an alternative embodiment of the invention, the cultivation medium may comprise the use of a cell suspension, which is obtained from single-cell fat production and which has fat still to be extracted.

For the purpose of growing a microorganism and/or producing fat, the cultivation medium can be supplemented with ingredients, which are other than those originating from a single-cell fat production process and which typically have an improving effect on a carbon to nitrogen ratio or on a trace element composition for enhanced growth and/or fat yield.

The invention can be implemented in accordance with any one of the embodiments, which embodiments are known to be favorable for creating microbial growth and producing fat of microbial origin. Thus, one preferred embodiment of the invention is the practical use of cell suspensions or side streams releasing from single-cell fat production processes for the production of fat particularly applicable as a component of transportation biofuel.

The microorganism with a capability of producing fat can be a yeast, algae or mold.

Preferred embodiments of the invention enable the use of one or more of the microorganisms listed as follows.

Fat-producing yeasts comprise, for example, those in the genera *Apiotrichum, Hansenula, Lipomyces, Rhodosporidium, Candida, Yarrowia, Rhodotorula, Sporobolomyces, Sporidiobolus, Trichosporon, Torulopsis, Waltomyces, Endomyces, Galactomyces, Pichia*, and *Cryptococcus*, such as *L. starkeyi, Rhodosporidium toruloides, Candida curvata, Y. lipolytica, Rhodotorula glutinis, Trichosporon cutaneum* and *Cryptococcus terricolus, Candida* sp. 107, *Lipomyces* sp. 33, *Rhodotorula gracilis, Trichosporon pullulans, T. fermentans, L. lipofera, Cryptococcus albidus*.

Fat-producing algae comprise, for example, those belonging to the genera *Ankistrodesmus, Astrionella, Attheya, Botryococcus, Brachiomonas, Characium, Chlamydomonas, Chlorella, Chlorococcum, Chromonas, Cryptomonas, Crypthecodinium, Cylindrotheca, Dunaliella, Gymnodinium, Euglena, Haematococcus, Isochrysis, Monallanthus, Nannochloris, Nannochloropsis, Navicula, Neochloris, Nitzschia, Ocromonas, Ourococcus, Pavlova, Phaeodactylum, Pleurochrysis, Prorocentrum, Prymnesium, Skeletonema, Stichococcus, Scenedesmus, Schizochytrium, Tetraselmis, Thalassiosira, Thraustochytrium* and *Ulkenia*, particularly *Botryococcus braunii, Brachiomonas submarina, Chlorella pyrenoidosa, C. protothecoides*, and *C. vulgaris, Crypthecodinium cohnii, Cylindrotheca* sp., *D. salina, E. gracilis, Isochrysis* sp., *M. salina, Nannochloris* sp., *Nannochloropsis* sp., *Navicula pelliculosa, Neochloris oleoabundans, Nitzschia leavis* and *N. palea, Ourococcus* sp., *Phaeodactylum tricomutum, Scenedesmus obliquus, Schizochytrium* sp., *Tetraselmis sueica* and *Ulkenia* sp.

A not fat-accumulating yeast, whose cells or cell residues can be used as a nutrient for fat-producing microorganisms, is for example *Saccharomyces cerevisiae*.

Fat production capable molds, dimorphic molds and filamentous fungi comprise, for example, the genera *Absidia, Aspergillus, Blakeslea, Chaetomium, Cladosporium, Claviceps, Clodosporidium, Cunninghamella, Emericella, Entomophthora, Fusarium, Gibberella, Glomus, Humicola, Mucor, Mortierella, Penicillium, Puccia, Pythium, Rhizopus, Saprolegnia, Trichoderma, Ustilago* and *Zygorhynchus*, such as molds of the genus *Absidia spinosa, Aspergillus*, for example *A. ficheri, A. flavus, A. nidulans, A. ochraceus, A. oryzae ja A. terrius, Blakeslea trispora, Chaetomium globosum, Cladosporidium herbarum, Claviceps purpurea*, molds of the genus *Cunninghamella*, for example *C. echinulata, C. japonica* and *C. elegans, Entomophthora coronata, Fusarium bulbigenum, Fusarium graminearum, Fusarium* sp., *Gibberella fujikuroi, Glomus caledonius, Humicola lanuginosa*, molds of the genus *Mucor*, for example *M. circinelloides, M. plumbeus* and *M. rouxii*, molds of the genus *Mortierella*, for example *M. isabellina, M. alpina* and *M. ramanniana*, molds of the genus *Penicillium*, for example *P. javanicum, P. lilacinum, P. spinulosum* and *P. soppii, Puccia coronata, Pythium ultimum, Rhizopus delemar, Rhizopus oryzae, Ustilago zeae, Zygorhynchus moelleri*, as well as *Malbranchea pulchella, Myrothecium* sp., *Sclerotium bataticola, Pellicularia practicola, Sphacelothea reiliana, Tyloposporidium ehren bergii, Achyla americana, Lepista nuda, Tilletia controversa, Cronartium fusiform*.

It is beneficial in the invention to use molds from the family Mucorales. It is particularly beneficial to use molds from the genera *Mucor, Mortierella, Cunninghamella* or *Aspergillus*.

The invention also enables the use of genetically modified microorganisms.

Fat-producing microorganisms are generally available from a range of microorganism culture collections. Fat-producing microorganisms and fat production processes have been described in literature, for example Ratledge and Wilkinson 1988 and 1989.

According to the present description, the cell suspension or residual cell mass from a single-cell fat production process, the autotrophically grown or mixotrophically and/or heterotrophically cultivated algal cell mass or residual cell mass can be used as a cultivation and fat production medium component for a fat-producing microorganism.

The fat production capacity of fat production capable microorganisms can be improved by carrying out the breakup of cell structures and/or the hydrolysis of ingredients with enzymes, such as β-1,3-glucanases, proteases, β-1,6-glucanases, mannanases and chitinases, or with enzymes-producing microorganisms. Enzymes suitable for the breakup of cell structures and/or for the hydrolysis of ingredients are produced for example by molds of the genera *Trichoderma* and *Aspergillus*, such as *T. reesei* and *A. niger*.

It is preferred that the second stage single-cell, preferably mold mass, left over after the extraction of fat, be further utilized for making components of side streams consisting of the cell mass and supernatant after the recovery of a second stage single-cell fat in accordance with the invention as starting materials for the production of single-cell fat or second stage single-cell fat. For this purpose, the components side streams can be used as such, or after a microbiological, enzymatic or chemical treatment or a combination of these treatments.

According to preferred embodiments of the present invention, practical use is made of residual cell mass obtained in a single-cell fat production process or liquid phase (supernatant) or a combination thereof.

According to another preferred embodiment of the invention, practical use is made of a cell suspension, which contains fat created in a single-cell fat production process.

Preferred embodiments of the invention provide a novel techno-economically more sustainable solution for the more comprehensive use of a single-cell mass containing organic material in order to produce single-cell fat, particularly for transportation biofuel, a raw material of biofuel, or components of these.

Preferred embodiments of the invention are depicted in the form of schematic views 1-7. In the schematic views, the main operations of prior art single-cell fat production processes are represented by a block diagram between vertical dashed lines ("Known single-cell fat production processes"), regarding sub-operations related to the present invention. The block diagram "Side stream fractions" presents fractions, which are released by the "known single-cell fat production processes" and which are within the scope of the present invention. Expressed more specifically, the side stream fractions refer to any aqueous solutions or supernatants releasing from the production of cells, the production of single-cell fat, the recovery of cells or the extraction of fat, and to a post-fat extraction mixture of variably broken and intact cells or residual cell mass. The block diagram under the term "Side stream processes" refers to operations included in the scope of the invention and applied to the above-mentioned side stream fractions, to the production of a microorganism, preferably mold mass, and a microorganism, preferably mold fat, and to the linkage of these masses with a known single-cell fat production process.

Consequently, the invention relates specifically to a method for the treatment of side stream fractions, a supernatant, and a post-fat extraction residual cell mass, all released from single-cell fat production, by means of microorganisms, especially molds, and to linking the treatment of a fat-containing second stage microorganism-based cell mass, formed as a result of the above treatments, with known single-cell fat production processes.

The method according to the invention also encompasses operations, in which the side stream fractions are supplemented with components which are beneficial from the standpoint of producing a second stage single-cell, especially mold mass and producing a second stage single-cell fat, especially mold-based fat.

The process according to the invention can be applied with the same embodiments also to side stream fractions other than just those originating from a single-cell fat production process, such as to organic-matter containing industrial or agricultural products or excess or side streams, to waste waters or community or household wastes, or to mixtures of these fractions and single-cell fat production process side streams, and the thus obtained single-cell fat containing second stage single-cell mass can be integrated to become a part of the "first stage" single-cell fat production process. Hence, the invention encompasses, in the capacity of "a side stream fraction", all organic-material containing fractions, which contain ingredients suitable for the growth of a microorganism, preferably mold, and for the production of fat either as such or supplemented with other nutrient components.

A typical feature of the invention is its applicability to the treatment of the side stream fractions of single-cell fat production processes with one or more microorganisms, preferably with mold. The side stream fractions of interest for the invention can be treated with one or more microorganisms, preferably with mold, either concurrently or in a successive sequence for establishing an effective microorganism growth and second stage single-cell fat yield in discrete microorganism processes (a second stage fat production process). It is also within the scope of the invention that the microorganism-based second stage residual cell mass or supernatant, left over after the extraction of a microorganism-based single cell fat resulting from the cultivation of a microorganism for the second stage fat production process, be further treated the same way as the treatment applied according to the present invention to the side streams of known single-cell fat production processes.

In the method according to the invention, it is found beneficial that a fat-producing microorganism, preferably mold, be used for treating the invention-concerned side stream fractions in accordance with several advantageous optional embodiments for providing the production of a second stage single-cell mass and the production of fat in the microorganism.

Preferred embodiments include also alternatives, according to which a side stream fraction is used in a way of preferably providing the production of a second stage single-cell mass, and the fraction is supplemented with components in a way of implementing the production of a second stage microorganism-based single-cell fat. Preferred components for use as supplements include hydrocarbons.

Another aspect in a preferred embodiment is selecting a side stream fraction, which is beneficial for the production of a second stage single-cell mass, and allowing then the second stage single-cell mass to produce fat with another side stream fraction either as such or supplemented with nutrients.

Preferred optional embodiments include also processes, in which, considering the practical use of side streams, the side stream and microorganism are selected as preferred from the standpoint of the production of a second stage single-cell mass and the hydrolytic activity of a microorganism, and the production of a second stage single-cell fat is implemented with another microorganism, the use of which is beneficial for converting the preceding hydrolysis products into the second stage single-cell fat.

It is within the scope of the preceding optional embodiment that the microorganism species function either as a mixed population or in discrete processes.

It is within all preferred alternatives of the invention that the second stage single-cell mass is recovered, the mass is subjected to the extraction of a single-cell fat with prior known methods, and the fat is used principally as transportation biofuel, as a raw material for biofuel, or as components of these, or for other applications, such as for a component of animal feed or foodstuffs.

Preferred embodiments of the method according to the invention include the formation of compositions as set forth below by using the optional treatments of side streams according to FIGS. 1-7 to serve as cultivation and fat production media for a microorganism, preferably mold, and for the production of fat.

Figure 6:
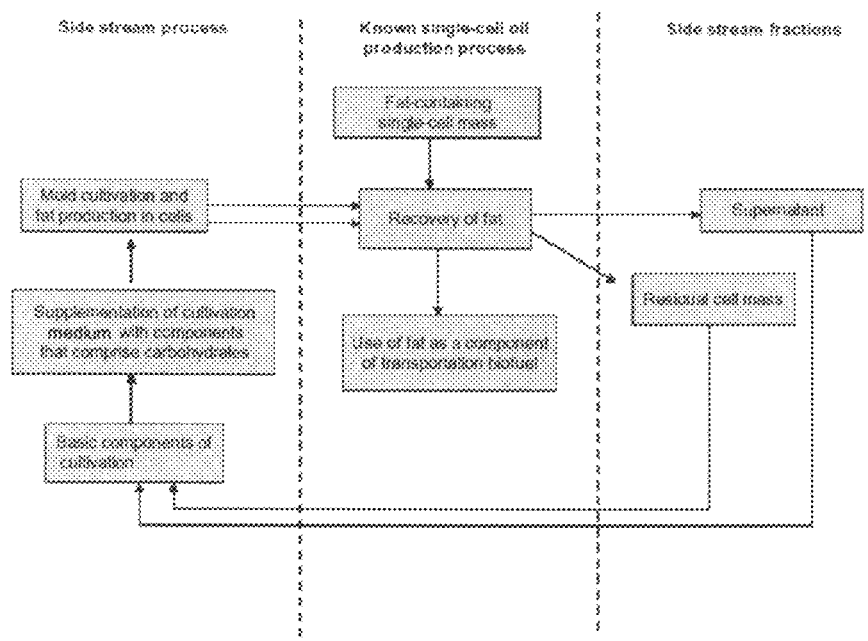
Figure 7:
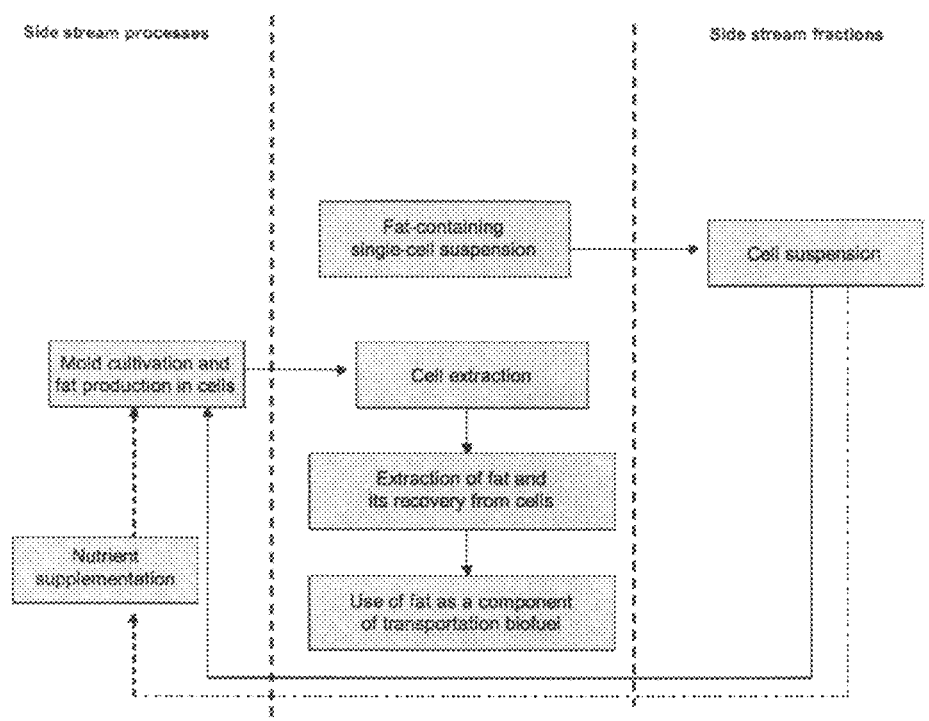

1. A composition, which is obtained by blending post-fat extraction residual cell mass with a supernatant (FIG. 1).
2. A composition, which contains some supernatant referred to in item 1, and a composition, which contains post-fat extraction residual mass, each with possible nutrient supplements (FIG. 2).
3. A composition, which has an ingredient of residual cell mass treated with acid or alkaline catalysts, or a composition, which contains both residual cell mass and residual cell mass treated with acid or alkaline catalysts (FIG. 3).
4. A composition, which contains residual cell mass treated with a microorganism and then subjected to a chemical treatment, or which alternatively contains a mixture of microorganism-treated residual cell mass and supernatant, which mixture is then subjected to a chemical treatment (FIG. 4).
5. A composition, which contains residual cell mass and/or supernatant, and which composition has been pretreated with a microorganism or with a mixture of microorganism cultures (FIG. 5).
6. A composition, which contains residual cell mass and/or supernatant and which has been complemented with mono-, oligo- or polymeric compounds, such as carbohydrates or mixtures thereof (FIG. 6).
7. A composition, which contains fat-containing single-cell mass without a preceding extraction of supernatant and fat, and which has optionally been supplemented with nutrients (FIG. 7).

One preferred embodiment of the invention is depicted in FIG. 1. According to this embodiment, the liquid phase in a cultivation medium for of a second stage single-cell fat, preferably mold-based fat production process comprises supernatant and/or supernatant supplemented with other liquid phases (from a first stage fat production process). The cultivation and fat production medium for a microorganism is established as the supernatant is supplemented preferably with residual cell mass. The residual cell mass comprises preferably post-fat extraction microalgae, yeast, a mixture thereof, or mold (from a first stage fat production process). The residual cell mass can have its microorganisms crushed in various ways and the residual cell mass may contain or can be supplemented with other ingredients. The invention does not single out a manner in which the cultivation and fat production of a microorganism in a second fat production stage is implemented, but the invention can be practiced with all techniques presented in literature and familiar to a skilled artisan. The invention can be practiced by varying the mutual relationships of residual cell mass and supernatant within a wide range, and it is within the context of the invention that the cultivation medium for a microorganism, preferably mold, can be supplemented with other nutrients. It is within the scope of the invention that, after the production of a second stage single-cell mass (microorganism biomass) and a single-cell fat (microorganism-based fat), the said biomass be delivered to a fat extraction process included in any prior art single-cell fat production process. The recovery of fat in primary and secondary fat production processes can be preferably carried out in a single unit process. Alternatively, the recovery of fat can be performed in discrete unit processes. The fat is preferably used as transportation biofuel, a raw material for biofuel, or as a component thereof.

The invention finds beneficial applications in several other embodiments, as well. In one preferred embodiment (FIG. 2), the cultivation and fat production medium for a microorganism, preferably mold, comprises supernatant and residual cell mass without blending the same together, such that both side streams can be processed regardless of each other or, if necessary, just one of the side streams can be utilized for optimizing energy and carbon balances for the process. This embodiment enables the selection of a microorganism useful for media comprising supernatant or residual cell mass separately of each other as necessary.

Figure 2:
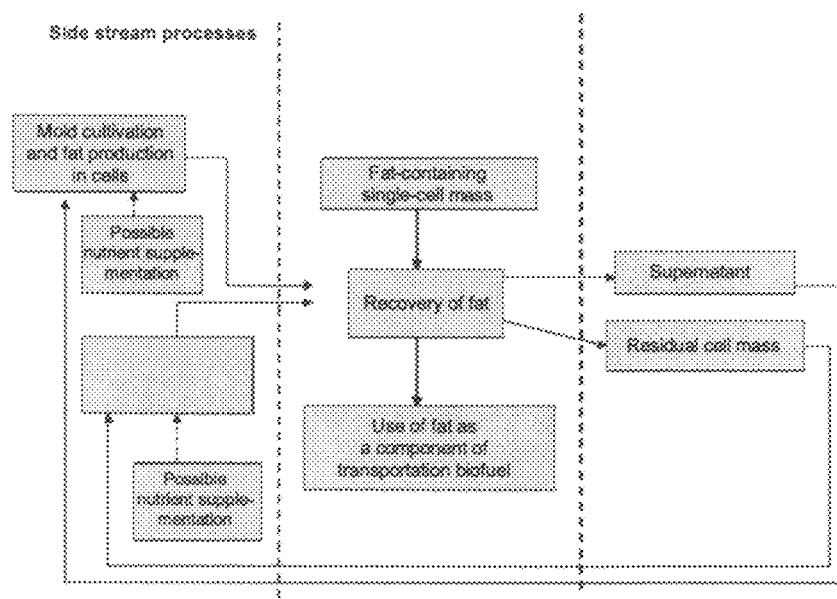

According to the invention, the process of FIG. 2 is capable of being linked as a part of any single-cell fat production process, in which the supernatant and the residual cell mass, as such or with nutrient supplements, are, in terms of the compositions thereof, adequate for the production of a second stage single-cell fat, typically a mold-based fat.

It is within the scope of the invention that the cultivation and fat production media, discussed therein and intended for a second fat production stage microorganism, such as mold, can be supplemented with side streams also other than those being released from single-cell fat production.

According to the invention, the second stage single-cell mass, typically mold mass, containing single-cell fat and resulting from the optional embodiments of FIG. 2, can be conducted to any single-cell fat production process and used as transportation biofuel, a raw material for transportation biofuel, or as a component of these.

Figure 3:
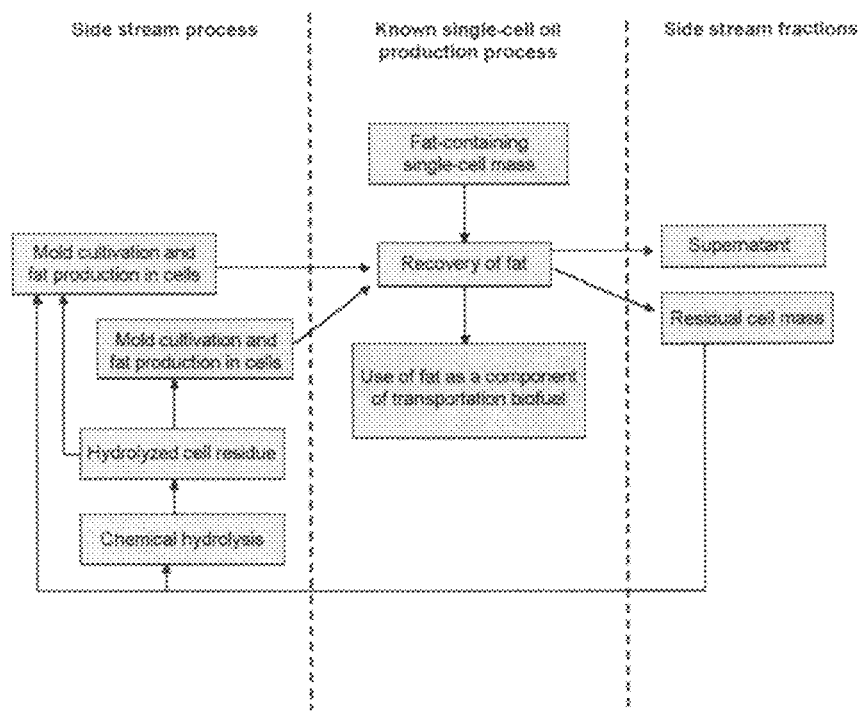
Figure 4:
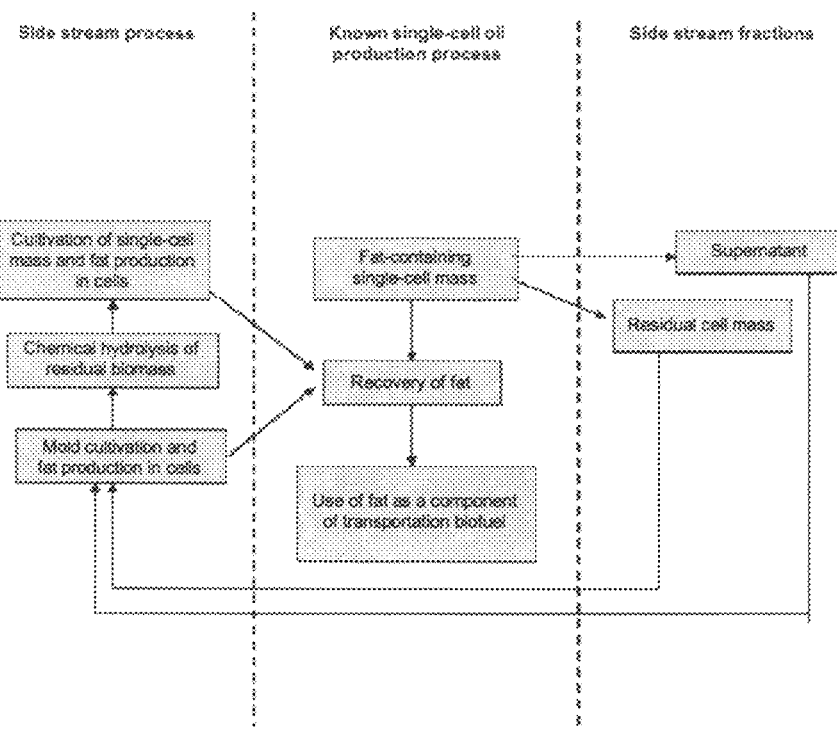

A preferred embodiment of the invention is also a single-cell fat production process, in which are included, as unit operations, a microbiological treatment and a chemical treatment of residual cell mass (FIG. 3). The invention is restricted neither to the order of conducting these two unit operations, nor to how many times these operations are carried out and the resulting order of conducting the same.

One preferred embodiment of the invention is also to process chemically treated and untreated residual cell masses into mixtures for producing a microorganism-, preferably mold-based fat. The residual cell masses may also originate from mutually independent single-cell fat production processes (first stage processes) and can be supplemented, as necessary, with components external of the residual cell masses. Most preferably applicable to the invention are residual cell masses of yeast and algal origin, preferably also biomasses, which do not directly originate from prior known single-cell fat production processes. Preferred residual cell masses comprise plant- and animal-based masses.

The chemical treatment is preferably conducted with acid, alkali, or both. The residual cell mass, treated with acid, alkali, or a mixture thereof, can be used as such for growing mold and producing fat, or it can be subjected to the removal of fractions prior to the mold treatment.

The process according to the invention does not limit constituent ratios used for unit operations, nor the numbers and order of conducting the treatments except in the sense that the cultivation medium made from the original residual cell mass is suitable for growing a microorganism, preferably mold, and for producing fat.

The process of FIG. 3 is preferably conducted by using supernatant, being released from prior known single-cell fat production processes, as a liquid phase or as a part of it.

The invention can be practiced also in an embodiment, in which the residual cell mass of a single-cell fat production process (first stage fat production process) and/or its supernatant are treated as a nutrient component for a microorganism, preferably mold growth, and the microorganism is allowed to grow and produce fat in a second stage fat production process, the fat is extracted according to any prior known single-cell fat production process, and the residual biomass, resulting from the activity of the microorganism in the second stage single-cell fat production process, is passed to a single-cell fat production process (first stage fat production process) after being chemically treated, preferably with chemical hydrolysis, and the result is further used for the production of single-cell mass and/or single-cell fat.

In this embodiment, as well as in the embodiment of FIG. 3, is naturally included an alternative that the result of a chemical treatment can be used as a component of the cultivation medium not only for growing mold but also for growing other microorganisms capable of using components created as a result of chemical hydrolysis and for the production of fat.

The process according to the invention is particularly suitable for implementation in an embodiment, comprising treating the residual cell mass, being released from single-cell fat production processes (first stage fat production process), so as to enable or enhance the growing of a microorganism and the production of single-cell fat, said microorganism accumulating fat in a second stage single-cell fat production process. This type of embodiment for the invention is depicted in FIG. 5 (FIG. 5).

Alternatively, the composition, comprising residual cell mass, can be treated concurrently in a mixed culture of microorganisms, preferably molds, thus accomplishing the above-described object according to the invention for the production of single-cell fat (microorganism-based fat).

Within the scope of the invention is preferably included an alternative that, in a second stage single-cell fat production process, in the growing of microorganisms, preferably molds, and in fat production, the liquid phase comprises supernatant of a single-cell fat production process (first stage fat production process).

Figure 5:
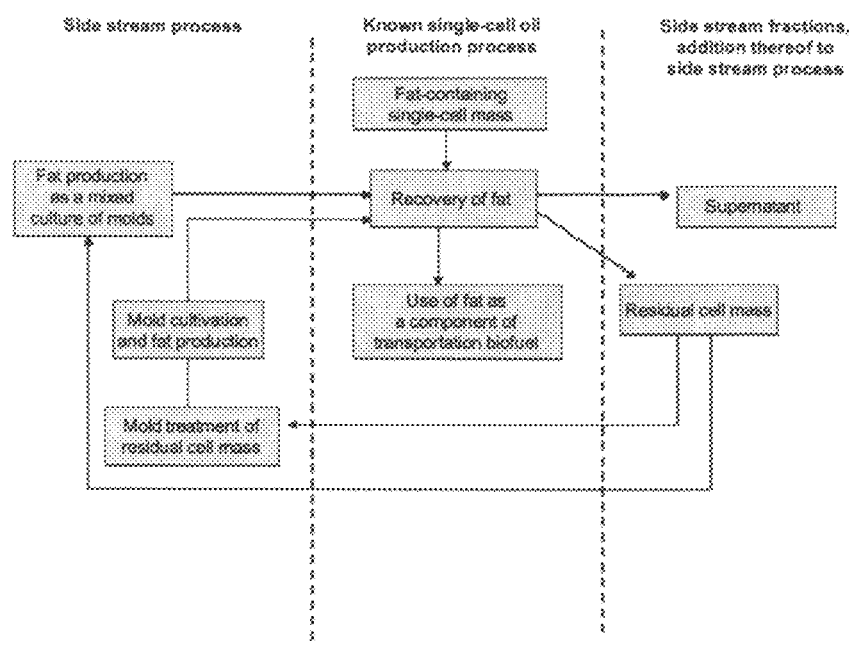

It is within the context of an optional embodiment of FIG. 5, included in the scope of the invention, that such embodiment can be implemented by applying also the optional embodiments of FIGS. 1-3, such as additions of external components, chemically treated residual cell mass or its fractions or residual cell masses originating from sources other than single-cell fat production processes.

Consequently, the optional embodiment of FIG. 5 introduces a solution, based on the use of more than one microorganism, preferably mold, in processes discussed in the context of FIGS. 1-3.

A preferred embodiment of the invention is that the microorganism, preferably mold cultivation and fat production medium, which is to contain residual cell mass or supernatant released from a single-cell fat production process (first stage fat production process) or of mixtures thereof for a second stage fat production process, be supplemented with components which have a special significance as a quantitative and qualitative source of biomass for transportation biofuel, a raw material for biofuel, or components thereof. FIG. 6 illustrates an embodiment of the invention beneficial in this respect.

The microorganism, preferably mold cultivation and fat production medium, containing residual cell mass or supernatant or mixtures thereof resulting from a single-cell fat production process for a second stage fat production process, is supplemented with components containing carbohydrates, such as starch, cellulose, lignocelluloses, mixtures thereof, or with components, in which the concentration thereof is favorable for promoting the growth of a microorganism, preferably mold, and/or the production of fat.

The embodiment according to the invention, shown in FIG. 6, is suitable for incorporation within any individual unit operations of the invention, as shown in FIGS. 1-5, or within any combinations thereof.

The method according to the invention encompasses such alternatives that the cultivation media discussed in reference to items 1-6 be supplemented with nutrient components favorable for the growth of a microorganism, preferably mold, for the production of fat, or both.

The method according to the invention can be applied to one or more side streams of single-cell fat production. Therefore, the invention also encompasses the ability of providing various combinations of the optional embodiments or parts thereof shown in FIGS. 1-6.

It is one of the preferred embodiments of the invention that the cultivation of a microorganism, preferably mold, the production of fat, and the recovery of a microorganism for the extraction of fat can be conducted with generally known embodiments and the thereby obtainable fat can be used as a component particularly in the manufacture of transportation biofuel. The invention can be preferably practiced also in such a way that the starting material is not residual cell mass and/or supernatant but, instead, a single-cell suspension which for various reasons has not been delivered to a prior known single-cell fat production process. (FIG. 7). Being composed of single-cell mass in a liquid and/or solid phase or single cell mass thereof broken in various degrees, this fraction can be passed according to the invention, as such or supplemented with nutrients, to the growing of a microorganism, preferably mold, and to the production of a second stage single-cell fat (microbial-based fat).

A particularly preferred feature of the invention is that the microorganism, preferably mold cultivation and fat production medium, the cell suspension, as discussed in reference to FIG. 7, can have associated therewith unit operations from among all unit operations according to diagrams 1-6 for growing a microorganism and producing a second stage single-cell fat (microorganism-based fat). The produced fat can be used principally as transportation biofuel, a raw material for biofuel, or as components of these for thereby promoting the overall use of biomass.

Particularly preferred are unit operations related to the invention, comprising the use of more than one microorganism, typically mold, either concurrently or as processes following each other.

It is an object of the following examples to illustrate the invention and shall not be construed as limiting the invention in any way.

EXAMPLES

Methods

Cultivation Media:

The general cultivation media for yeasts and molds involved the use of culture media as follows. The YPD or yeast-peptone-dextrose cultivation medium comprised, as per liter of supernatant, 10 g yeast extract, 20 g peptone, and 20 g glucose. The composition of PDA or potato dextrose agar per liter of water was 4.0 g potato extract, 20.0 g dextrose, and 15.0 g Agar No. 1. The composition of MPA or malt extract peptone agar per liter was 30 g malt extract, 3 g bactopeptone, and 15 g Agar No. 1.

Hydrolysis of Biomasses:

In order to hydrolyze carbohydrates contained in a biomass, the biomass was treated with 1.33 M sulphuric acid at a temperature of 95° C. for a period of 4 h in a closed vessel. For one gram of biomass, there was added 3 ml sulphuric acid in solution. The reaction was followed by neutralizing the mixture with an equivalent amount of $CaCO_3$. This was followed by the addition of water for dissolving the sugars in water. In order to analyze the sugars, an internal standard, xylitol (about 1 mg/ml), was added into hydrolysis samples. From hydrolysate was extracted a short amount of solution (1 ml), which was centrifuged, and from the clear liquid was extracted an HPLC sample.

Sugar Definition:

In order to define the sugar concentration of a solution, the solution was made into a suitable dilution which was filtered through 0.2 µm prior to an HPLC analysis.

The column used in sugar definition was Shodex Sugar SP 0810 ion-exchanger in lead form (in stationary phase). The column dimensions were 8.0 mm (ID)×300 mm. The eluent was water (flow rate 0.6 ml/min) and the column temperature was 60° C. The detector was RI Shimatzu RID 10A and the pump was A6 and the autosampler was Shimatzu SIL 20A. The processing of results was conducted with Class-VP software.

Fatty Acid Analysis:

The fatty acid composition of samples was determined as in the method described by Suutari et al. (1990). Lipids in the samples were first hydrolyzed into free fatty acids, which were saponified into sodium salts thereof and thereafter methylated into methyl esters. The fatty acid methyl esters were analyzed gas chromatographically.

Microorganism Strains

Fat-producing microorganisms are generally available from a plurality of strain collections, such as ATCC, DSM, etc. Various embodiments of the invention are discussed in the following examples by using microorganism strains as follows. *Mucor circinelloides* (DSM 1175), *Mortierella isabellina* (DSM 1414) and *Trichoderma reesei* (TKK 2021).

Example 1

It was studied how the growth of mold is influenced by a liquid residue, a supernatant, resulting from a yeast-based single-cell fat production process, as it is substituted for water in an YPD cultivation medium commonly used for mold.

The supernatant comprised a supernatant resulting from growing the yeast *Lipomyces starkeyi* and from fat production. The cultivation medium was sterilized by autoclaving at 120° C. for 15 min. The cultivations were conducted in 250 ml Erlenmeyer flasks with a cultivation medium of 50 ml in volume.

The effect on two mold types was assessed. For this purpose, parallel cultivation medium flasks were inoculated with 500 µl of the spore suspension *Mortierella isabellina* and, respectively, parallel cultivation medium flasks with 500 µl of the spore suspension *Mucor circinelloides*. The cultures were incubated at a temperature of 28° C. in a shaker with a mixing speed of 160 rpm. During cultivation, the *M. circinelloides* cultures were supplemented, 2 days after the incubation, with 1 g dextrose monohydrate.

For the sake of comparison, *M. isabellina* mold was cultivated on an YPD medium of the above-described type, in which the yeast-growing medium was replaced with tap water. Other than that, the cultivation proceeded the same way as in the case of an YPD culture prepared for a yeast cultivation supernatant. As opposed to this, the latter YPD culture was supplemented, 4 days after the incubation, with 2 g dextrose monohydrate. Respectively, the growth of *M. circinelloides* mold was assessed in an YPD cultivation medium prepared in tap water. The *M. circinelloides* culture was supplemented with 1 g dextrose monohydrate 3 days after the incubation.

Molds were found to produce significant amounts of biomass by using a yeast-based supernatant as a base for the cultivation medium. *M. isabellina* mold produced dry matter with a fat content of 33%, 7.6 g/l over 2 days of incubation. As incubation was continued, the dry matter content increased and was 16 g/l after 3 days of incubation, the dry matter having a fat content of 32%.

When the yeast-based supernatant was replaced with tap water, *M. isabellina* mold produced, over 4 days of incubation, 20 g/l dry matter with a fat content of 20%. It was not until the first addition of dextrose and 7 days of incubation that the fat content of mold mass had risen to 39% (of dry matter), at which time the amount of dry matter produced by mold was 28 g/l.

A yeast-based supernatant was found to enhance significantly the ability of *M. isabellina* mold to produce fat in this particular cultivation medium as the mold also produced fat about 30% of its dry matter, even though, in calculation, the above-described YPD medium of yeast extract, peptone and glucose is not optimal from the standpoint of fat production, the carbon to nitrogen ratio being 6.6. Respectively, when using tap water as a base for the cultivation medium, the fat content of mold remained as low as 20% of dry matter unless dextrose was added into the cultivation medium. It was also found that, in a yeast-based supernatant containing medium, *M. isabellina* mold had progressed to fat production remarkably faster than in a tap water-based YPD medium, because, in a cultivation medium composed of a yeast growing supernatant, the discussed mold produced more than 30% fat of its dry matter as rapidly as over 2 days of incubation, whereas in an YPD medium made in tap water, the mold did not begin to produce fat in a meaningful amount until after the glucose addition.

*M. circinelloides* mold was also found to grow in an YPD cultivation medium prepared in a yeast-based supernatant equally well compared to its growth in a tap water-based YPD cultivation medium. In the cultivation medium based on a supernatant of yeast, this particular mold grew to the same dry matter content of 25 g/l after 2 days of incubation as in the tap water-based YPD cultivation medium after a glucose addition and 4 days of incubation.

Example 2

*Lipomyces starkeyi* yeast was used, in accordance with a known single-cell fat production process, for the production of fat and the supernatant obtained from this process was used as a mold cultivation medium. The supernatant was sterilized by autoclaving at 120° C. for 15 min. The cultivations were conducted in 250 ml Erlenmeyer flasks with a cultivation medium of 50 ml in volume.

Parallel flasks containing cultivation medium were inoculated with 500 µl of the spore suspension *Mortierella isabellina* and, respectively, parallel cultivation medium flasks with 500 µl of the spore suspension *Mucor circinelloides*. The cultures were placed for incubation at a temperature of 28° C. in a shaker with a mixing speed of 160 rpm.

The *M. circinelloides* cultures were supplemented, after 2 days of incubation, with 1 g dextrose monohydrate. Respectively, the *M. isabellina* cultures were supplemented with 1 g dextrose monohydrate after 3 days of incubation.

After the glucose addition, the amount of fat produced by *M. isabellina* in a yeast-based supernatant was 85% of the dry matter. *M. circinelloides* produced nearly 20% fat even before the addition of sugar. When using a yeast-based supernatant and added glucose, the amount of dry matter produced by the molds is 3-9 g/l.

| Mold | days | Dry content (g/l) | Fat content of dry mold mass (%) |
|---|---|---|---|
| M. isabellina | 2 | 2.8 | |
| M. isabellina | 3 | 8.3 | 6.8 |
| M. isabellina | 6 | 8.8 | 85 |
| M. circinelloides | 2 | 4.3 | 18 |
| M. circinelloides | 3 | 5.3 | 24 |
| M. circinelloides | 6 | 4.6 | 30 |

The results indicate that a supernatant, releasing from a yeast-based prior known single-cell fat production process, makes as such a favorable mold cultivation medium, in which the fat yield of mold can be further enhanced by a mere carbohydrate addition into the cultivation medium.

Example 3

The *Brachiomonas submarina* algal suspension, which had been cultivated heterotrophically by using glucose as a carbon source, was subjected to the extraction of cells for the recovery of single-cell fat, and the leftover cultivation liquid, a supernatant, was used for preparing a cultivation medium for mold by adjusting it to a pH value of 5.5 with NaOH. The supernatant was sterilized by autoclaving at 120° C. for 15 min.

*Mortierella isabellina* and *Mucor circinelloides* molds were used for the preparation of spore suspensions. In order to prepare a spore suspension, the germinating PDA Petri dish culture of each mold was supplemented with 9 ml sterile water, the spores being released therein by means of an angle wand. For each mold, the algal supernatant was used to prepare parallel 50 ml cultivation media which were inoculated with 500 µl of the above-mentioned spore suspension. The mold cultures were incubated at a temperature of 28° C. in a shaker with a mixing speed of 160 rpm. Samples picked up from the cultivations were filtered and washed with distilled water. The filtration was followed by drying the samples overnight at a temperature of about 70° C.

The *M. isabellina* mold had a dry matter content of 0.8 g/l after 5 days of incubation and at this point the dry mold mass had a fat content of 13%. The *M. circinelloides* mold had a dry matter content of 1.3 g/l and a fat content of 16% in the *Brachiomonas* cultivation medium after 5 days of incubation.

The results indicate that a supernatant, releasing from microalgae-based single-cell fat production, makes as such a mold cultivation and fat production medium.

Example 4

The *Chlorella pyredoinosa* algal suspension, which had been cultivated heterotrophically by using glucose as a carbon source, was subjected to the extraction of cells by filtration for the recovery of single-cell fat. The leftover cultivation liquid, a supernatant, which was glucose-fee on the basis of a sugar definition analysis set forth in the method section, was used as a cultivation medium for molds. The supernatant was sterilized by autoclaving at 120° C. for 15 min. The mold cultivations were conducted in a 50 ml cultivation medium volume in 250 ml Erlenmeyer flasks.

Assessment was conducted on the growth of two molds with a *Chlorella* supernatant. For this purpose, parallel cultivation medium flasks were inoculated with 500 µl of the spore suspension *Mortierella isabellina* and, respectively, parallel cultivation medium flasks with 500 µl of the spore suspension *Mucor circinelloides*. The spore suspensions used as mold inoculants had been prepared by suspending the spores of a PDA Petri dish-cultivated germinating mold culture in 12 ml of sterile water. The mold cultures were incubated at a temperature of 28° C. in a shaker with a mixing speed of 160 rpm. Samples picked up from the mold cultures for dry matter and fat content assessments were filtered for the extraction of mold mass through a Whatman 3 filter and washed with distilled water. The samples were dried at a temperature of 60° C. and ground before a fatty acid analysis.

When using the *Chlorella pyredoinosa* supernatant as a cultivation medium, the *M. isabellina* mold produced, over 8 days of incubation, 0.4 g/l of dry matter with a fat content of 27%. Respectively, the *M. circinelloides* mold grew to a 1.1 g/l dry matter content, having a fat content of 4.4%.

The results indicate that a supernatant, releasing from microalgae-based single-cell fat production, makes as such a mold cultivation and fat production medium.

Example 5

A study was conducted on how the growth of mold is influenced by a liquid residue, a supernatant, resulting from a yeast-based single-cell fat production process, as it is substituted for water in an YPD cultivation medium commonly used for mold.

The supernatant comprised a supernatant resulting from the cultivation of *Chlorella pyredoinosa* algae and the production of fat by using glucose heterotrophically as a carbon source. The supernatant had resulted from the algal suspension after the extraction of cells conducted for the recovery of single-cell fat by filtration, and on the basis of a sugar assessment analysis described in the method section, the supernatant was glucose-free.

The cultivation medium was sterilized by autoclaving at 120° C. for 15 min. Cultivations were conducted in 250 ml Erlenmeyer flasks with a cultivation medium of 50 ml in volume.

An assessment was conducted on the growth of two molds in an YPD cultivation medium prepared in a *Chlorella* supernatant. For this purpose, parallel cultivation medium flasks were inoculated with 500 µl of the spore suspension *Mortierella isabellina* and, respectively, parallel cultivation medium flasks with 500 µl of the spore suspension *Mucor circinelloides*. The spore suspensions used as mold inoculants had been prepared by suspending the spores of a PDA Petri dish-cultivated germinating mold culture in 12 ml of sterile water. The mold cultures were incubated at a temperature of 28° C. in a shaker with a mixing speed of 160 rpm. During cultivation, the *M. isabellina* mold cultures were supplemented with 2 g dextrose monohydrate 3 days after incubation. Samples picked up from the mold cultures during cultivation for dry matter and fat content assessments were centrifuged for the extraction of mold mass, and the mold mass was washed with distilled water. The samples were cold dried and the fatty acid composition was analyzed as set forth in the method section.

In the YPD cultivation medium prepared with a *Chlorella pyredoinosa* supernatant, the *M. isabellina* mold grew, over 2 days of incubation, to a dry matter content of 9.9 g/l. After the glucose addition, the mold grew, over 8 days of incubation, to a dry matter content of 32 g/l, the dry matter having a fat content of 27%. Respectively, in this particular cultivation medium, the *M. circinelloides* mold grew, over 2 days of incubation, to a dry matter content of 15 g/l.

The results indicate that a supernatant, releasing from microalgae-based single-cell fat production, is applicable, when supplemented with other nutrients, for use as a mold cultivation and fat production medium.

Example 6

*Mortierella isabellina* and *Mucor circinelloides* molds were inoculated onto a cultivation medium, having its carbon source consisting of one of the following components:

1. *Lipomyces starkeyi* Cell Mass Prior to Fat Extraction

The cell concentrate of *Lipomyces starkeyi* yeast was used to prepare a cultivation medium in tap water, which contained yeast mass with a dry fat content of 30 g/l. The dry yeast mass had a fat content of 50%. The cultivation liquid had its pH adjusted to the value 5.5 with NaOH. The medium was sterilized by autoclaving at 121° C. for 15 min.

*Mortierella isabellina* and *Mucor circinelloides* molds were used for the preparation of spore suspensions. In order to prepare a spore suspension, the germinating PDA Petri dish culture of each mold was supplemented with 9 ml sterile water, the spores being released therein by means of an angle wand. Each mold was subjected, on the algal medium, to parallel 50 ml cultivations which were inoculated with 500 µl of the above-mentioned spore suspension.

The mold cultures were incubated at a temperature of 28° C. in a shaker with a mixing speed of 160 rpm. Samples picked from the cultivations were filtered and washed with distilled water. The filtration was followed by drying the samples overnight at a temperature of about 70° C.

With a cultivation medium containing solely *Lipomyces* cell mass, the *M. circinelloides* mold grew, over 5 days of incubation, to a dry matter content of 6.1 g/l and at this point the mold dry matter had a fat content of 57%. The *M. isabellina* mold grew on *Lipomyces* cell mass over 11 days to a dry matter content of 4.3 g/l, and *M. circinelloides* mold to a dry matter content of 8.4 g/l.

Thus, the fat-containing yeast mass is applicable as such to growing molds and producing mold fat.

The *Lipomyces starkeyi* cell mass, which had been treated according to a known single-cell fat production process and supplemented with minerals.

The dried glucose-cultivated *Lipomyces starkeyi* yeast cell mass with a residual fat content of 36% was used to prepare a cultivation medium in tap water. The cultivation medium had a composition per liter of water as follows: 25 g dried *Lipomyces starkeyi* yeast cell mass; 1.0 g $MgSO_4.7H_2O$; 0.7 g $K_2HPO_4.3H_2O$; 1.0 g $KH_2PO_4$; 0.2 g $CaCl_2.2H_2O$. Before its use, the yeast mass had been first dried, ground in a mortar, leached with dichloromethane, ground again and leached again. After this, the cell mass had still been comminuted with a Fritz pulverisette mill (0.5 mm filter) and leached for the extraction of fats with dichloromethane overnight, whereafter the residue mass had been stripped of solvent residues by evaporation. The cultivation medium was sterilized by autoclaving at 121° C. for 15 min.

Spore suspensions were prepared from *Mortierella isabellina* and *Mucor circinelloides* PDA cultures. The germinating Petri dish cultures of molds were supplemented with 9 ml of sterilized water and the spores were suspended in water by means of an angle wand. Thus prepared *M. isabellina* and *M. circinelloides* spore suspensions were inoculated with 500 µl into 50 ml parallel cultivation medium batches and the cultures were incubated at a temperature of 28° C. while shaking at 160 rpm.

Samples picked up from the cultures were filtered through a cellulose fiber filter for the removal of yeast cells, and the mold mass was washed several times with distilled water. The samples were dried at a temperature of 70° C.

After 10 days of incubation, as a result of microscoping with a phase contrast microscope by using a total magnification of 100 to 1000 times (Nikon Labophot 2, Japan), it was concluded that the *M. circinelloides* mold had taken and stored in itself the fat from yeast cells which contained fat as the growing was started. Parts of the mold hyphae were rich in fat, a conclusion which was based on the large number and size of fat globules evolved in the mold hyphae. After 11 days of incubation, the *M. circinelloides* mold mass had a dry matter content of 6.0 g/l and the mold mass had a fat content of 35%.

After 16 days of incubation, it was concluded by microscoping that the *M. isabellina* mold had also grown on a medium, which consisted of *Lipomyces starkeyi* cell mass, supplemented with minerals, treated in view of removing intracellular fat. Based on microscoping, the mold had accumulated, during cultivation, a small amount of fat, which was concluded on the basis of a few, not particularly large fat globules evolved in the mold hyphae.

2. *Lipomyces starkeyi* Cell Mass, which had been Treated for the Extraction of Intracellular Fat.

Because it was clearly indicated that molds, supplemented with nutrients, are capable of using the residual cell mass of yeast for the growth thereof and for the production of fat, the corresponding tests were conducted without nutrient supplements. Therefore, a cultivation medium was prepared in tap water, said medium containing 25 g/l dried glucose-cultivated *Lipomyces starkeyi* yeast cell mass with a fat content of 36%. Prior to use, the mass had first been dried, ground in a mortar, leached with dichloromethane, ground again, and leached again. After this, the mass had still been comminuted with a Fritz pulverisette mill (filter 0.5 mm) and leached overnight with dichloromethane for the extraction of fats, after which the residual mass had been stripped of solvent residues by evaporation. The cultivation medium was sterilized by autoclaving at 121° C. for 15 min.

Spore suspensions were prepared from germinating PDA Petri dish cultures of *Mortierella isabellina* and *Mucor circinelloides* molds. The Petri dishes were supplemented with 9 ml of sterilized water and the spores were suspended in water by means of an angle wand. Each spore suspension was inoculated with 500 µl into 50 ml parallel cultivation medium batches and the cultures were incubated at a temperature of 28° C. while shaking at 160 rpm.

The *M. circinelloides* mold grew, after 11 days of incubation, to a dry matter content of 7.3 g/l. At this point, the dry mold mass had a fat content of 20%.

It was found by microscoping, after 16 days of incubation, that the *M. isabellina* mold had grown and accumulated fat during cultivation, a conclusion which was made on the basis of fat globules developed in mold hyphae. Accordingly, the residual cell mass of a yeast-based known single-cell fat production process is applicable, even as such, for the cultivation of mold and for the production of mold-based fat.

4. *Rhodosporidium toruloides* Residual Cell Mass Supplemented with Minerals

The yeast cell mass used for a mold cultivation medium was extruded and once dichloromethane-leached, glucose-cultivated *Rhodosporidium toruloides* mass. The cultivation medium had a composition per liter water as follows: 60 g *Rhodosporidium toruloides* yeast cell mass; 1.0 g yeast extract; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The medium was homogenized with an Ultra Turrax device and sterilized by autoclaving at 121° C. for 15 min.

A spore suspension to serve as the inoculants was prepared from a germinating MPA Petri dish culture of *Mortierella isabellina* mold. The Petri dish was supplemented with 9 ml of YPD liquid and some spore was removed by scraping the vegetation surface with an inoculation loop. Thus prepared spore suspension was inoculated with 300 µl into parallel 50 ml cultivation media. The inoculated liquids were incubated at a temperature of 26° C. first for 2 days and then at a temperature of 28° C. The cultivations were conducted as shaking cultivations and the shaking rate was 160 rpm.

Samples were picked up from the parallel cultures in order to concentrate mold cells from yeast mass by centrifuging and washing samples with water. Samples were centrifuged by applying speeds over the range of 800 to 6000 rpm and centrifuging times of 2 to 10 minutes. The objective was to strip the samples as thoroughly as possible of yeast cells and cell residues left in the supernatant. The samples were stored in deep freeze and cold-dried prior to a fatty acid analysis.

When using broken *R. toruloides* yeast mass as a carbon source, it was found, after 1 day of incubation, that the cultivation liquid had a red layer of fat on its surface. On the basis of cultivation liquid control, the layer of fat was concluded to develop without the effect of mold with loose fat in the yeast mass slowly accumulating together. However, the layer of fat disappeared during 2 days of incubation. This enabled a conclusion that free fat was consumed by mold, because fat did not vanish from the control test.

The *M. isabellina* mold germinated on a medium of *R. toruloides* yeast over 1 day of incubation, which was verified e.g. by way of medium-developed mold pellets as well as by microscoping. Based on microscoping, it was found that the mold had started the accumulation of fat during 7 days, which was concluded on the basis of fat globules developed in mold hyphae.

After 8 days, the medium of yeast mass indicated, after fractionating, that the mold had a dry matter content of about 16 g/l. The mold fraction had a fat content of 33%.

Based on the test, it can be concluded that residual cell masses, resulting from yeasts that are used in known single-cell fat production processes, are suitable for the cultivation of mold and for the production of mold-based fat.

Example 7

*Lipomyces starkeyi* yeast mass, originating from a known single-cell fat production process, was blended with a supernatant resulting from a similar process. The mixture was inoculated with mold, and the mold was allowed to grow and produce fat.

A cultivation medium was prepared by suspending dry residual yeast cell mass, treated for the extraction of fats, 25 g per liter of supernatant obtained from the single-cell fat production process. The employed supernatant was a *Lipomyces starkeyi* glucose-cultivation supernatant, which had been stored by deep-freezing and which contained dry matter 43 V. On the basis of conducted sugar analyses, described in the methods section, the cultivation medium had a glucose content of 0 g/l. The employed residual cell mass consisted of glucose-cultivated *Lipomyces starkeyi* yeast mass, which had been treated according to a known single-cell fat production process for the elimination of fat. The yeast mass had a fat content of 36%. The cultivation liquid had its pH adjusted with 2 M NaOH to the value 5.9. The adjustment was followed by a homogenization of the medium with an Ultra Turrax device at a low speed of rotation. The cultivation medium was sterilized by autoclaving at 121° C. for 15 min.

From a germinating PDA Petri dish culture of *Mortierella isabellina* was prepared a spore suspension. The Petri dish was pipetted with 12 ml sterile water and the culture was stripped of spores in the liquid by means of an angle wand. The *M. isabellina* spore suspension/spore suspensions, prepared as described above, was/were inoculated with 500 µl into parallel 50 ml cultivation media. The cultures were placed to incubate at a temperature of 28° C. while mixing at 160 rpm.

Samples were picked up from the mold cultures, which were filtered through a cellulose fiber filter and washed with abundant, about 250 ml distilled water. The samples were dried either in oven at a temperature of 70-95° C. or in a cold dryer. The oven-dried samples were comminuted in a mortar prior to a fatty acid analysis.

When the employed cultivation medium consisted of leached *Lipomyces starkey* yeast mass, suspended in a supernatant resulting from a single-cell fat production process, the *M. isabellina* mold mass had a dry matter content of 7.4 g/l after 9 days of incubation, at which point the dry mold mass had a fat content of 40%.

Tests indicated that cultivation media, which contained combinations of a residual cell mass of yeast and a supernatant, are the most effective in working as factors promoting both the growth of mold and the fat production of mold. The test indicates especially that with molds, which grow weakly on residual cell mass alone and thus produce little fat, a major improvement can be provided by combining both supernatant and residual cell mass as components for a cultivation medium.

Example 8

1. Dried *Saccharomyces cerevisiae* Yeast Mass as a Carbon Source

The goal was to verify that yeasts, which inherently do not accumulate fat, can function as factors promoting the growth of mold and the production of mold fat.

In tap water was prepared a cultivation medium, containing 25 g/l dried *Saccharomyces cerevisiae* yeast mass. The medium had a pH of 6.25. The employed *Saccharomyces cerevisiae* baker's yeast consisted of fresh yeast (Fresh yeast, Finnish Yeast Ltd., Finland), which had been dried in oven overnight (50-80°). The medium was sterilized by autoclaving at 121° C. for 15 min.

From *Mortierella isabellina* and *Mucor circinelloides* PDA Petri dish cultures were prepared spore suspensions. The Petri dishes were pipetted with 12 ml sterile water and the spores were suspended in water by means of an angle wand. 500 µl of thus prepared *M. isabellina* spore suspension was pipetted into parallel 50 ml cultivation media. Respectively, 500 µl of *M. circinelloides* spore suspension was inoculated into parallel 50 ml cultivation media. The cultures were placed to incubate at a temperature of 28° C. while mixing at 160 rpm.

From the mold cultures were picked up samples, which were filtered by using a cellulose fiber filter and washed with abundant water (about 250 ml distilled water). The samples were dried either in oven at a temperature of 70-95° C. or in a cold dryer. The oven-dried samples were comminuted in a mortar and from the samples were weighed fatty acid analysis samples for kimax tubes.

On a cultivation medium, containing solely *Saccharomyces cerevisiae* yeast mass, the *M. circinelloides* mold grew, over 14 days of incubation, to a dry matter content of 2.6 g/l, the mold having a fat content which was very low (0.3%). *M.*

*isabellina* was clearly weaker in its growth on the *Saccharomyces cerevisiae* medium. On this particular medium, the dry matter content of *M. isabellina* mold remained over 9 days of incubation as low as 1.5 g/l, the mold having a fat content of 15%. Continued incubation did not increase the dry matter yield and, after 14 days of incubation, the content of dry mold matter was 1.0 g/l and its fat content was 12%. The employed yeast mass had a fat content of 8%, indicating that some fat had been produced by mold from the yeast mass.

The results show that unbroken yeast mass with a very low fat content is functional as a mold cultivation medium. The observation, according to which the fat amount of mold became higher than the fat amount of yeast mass used in the cultivation medium, demonstrates that mold itself was able of synthesize fat from the employed yeast mass.

2. Dried *Saccharomyces cerevisiae* Yeast Mass and a Supernatant Obtained from *Lipomyces Starkeyi* Cultivation as Cultivation Medium Components A cultivation medium was prepared for mold by slurrying 25 g/l dried *Saccharomyces cerevisiae* yeast mass not in tap water but, instead, in a cultivation medium supernatant obtained from *Lipomyces starkeyi* yeast cultivation. The employed baker's yeast consisted of fresh yeast (Fresh yeast, Finnish Yeast Ltd., Finland), which had been dried in oven overnight (50-80° C.). The yeast supernatant employed in the medium originated from a known single-cell fat production process, in which the employed carbon source had been glucose and the employed organism had been *Lipomyces starkeyi* yeast. The medium's pH was adjusted from the value of about 5.2 to the value of 5.8 by using 2 M NaOH. The medium was sterilized by autoclaving at 121° C. for 15 min.

From the *Mortierella isabellina* and *Mucor circinelloides* PDA Petri dish cultures were prepared spore suspensions. The Petri dishes were pipetted with 12 ml sterile water and the spores were suspended in water by means of an angle wand. 500 µl of thus prepared *M. isabellina* spore suspension was pipette into parallel 50 ml cultivation media. Respectively, 500 µl of *M. circinelloides* spore suspension was inoculated into parallel medias. The cultures were placed to incubate at a temperature of 28° C. while mixing at 160 rpm.

Samples picked up from the mold cultures were filtered and washed with abundant water (about 250 ml distilled water). The samples were dried either in oven at a temperature of 70-95° C. or in a cold dryer. The oven-dried samples were comminuted in a mortar and from the samples were weighed fatty acid analysis samples into kimax tubes.

On a cultivation medium, containing *Saccharomyces cerevisiae* yeast mass and *Lipomyces* supernatant, the *M. circinelloides* mold grew over 14 days of incubation to a dry matter content of 11 g/l and the fat content of the mold rose to 8.7%. Respectively, on this particular medium, the *M. isabellina* mold grew over 9 days of incubation to a dry matter content of 4.4 g/l, the dry mold mass having a fat content of 40%.

The results indicate that the supernatant enhances the ability of mold to grow and produce fat on a cultivation medium that contains whole yeast cells.

3. Dried *Saccharomyces cerevisiae* Yeast Mass (Whole Cells) Supplemented with Salts It was demonstrated that the addition of minerals as a nutrient and principal carbon source in mold cultivation provides an enhancing effect on the growth of molds when using yeast which does not inherently produce fat.

In tap water was prepared a cultivation medium with a composition per liter of water as follows: 25 g dried *Saccharomyces cerevisiae* yeast mass; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The employed baker's yeast consisted of fresh yeast (Fresh yeast, Finnish Yeast Ltd., Finland), which had been over-dried overnight (50-80° C.). The cultivation medium was homogenized with an Ultra Turrax device and sterilized at a temperature of 121° C. for 15 min. The mold cultivations were conducted in 250 ml Erlenmeyer flasks in a 50 ml cultivation medium volume.

The employed *Mortierella isabellina*, *Mucor circinelloides* and *Trichoderma reesei* mold inoculants were spore suspensions, which were prepared by supplementing the germinating PDA Petri dish cultures of the above-mentioned molds with 12 ml sterile water and by releasing the spores within the water by means of an inoculation loop. *M. isabellina* and *M. circinelloides* molds were inoculated into 50 ml cultivation media in the amount of 500 µl. In addition to this, two cultivation media were inoculated with both *M. isabellina* and *T. reesei* spore suspensions for a mixed culture in one and the same cultivation medium, both in the amount of 500 µl. The mold cultures were incubated at a temperature of 28° C. in a shaker with a mixing rate of 160 rpm. Samples picked up from the mold cultures were filtered, washed with distilled water, and dried for about 1 day at a temperature of about 60-70° C.

On a cultivation medium, which contained *S. cerevisiae* yeast, the *M. circinelloides* mold produced 5.7 g/l dry matter over 7 days of incubation. Respectively, the dry matter content of *M. isabellina* mold was 1.3 g/l after 7 days of incubation. The use of a mixed mold culture enhanced the activity of *S. cerevisiae* mass and, in the mixed culture of *M. isabellina* and *T. reesei* molds, the amount of dry mold matter created over 8 days of incubation was 3.1 g/l.

The results indicate that a residual biomass-based cultivation medium can be supplemented with other growth components, such as salts, for thereby enhancing and accelerating the production of mold biomass with respect to a cultivation medium not containing nutritional supplements.

4. Dried *Saccharomyces cerevisiae* Yeast Mass Supplemented with Salts and Glucose The objective was to demonstrate that yeasts, which do not inherently accumulate fat, may function as contributors to mold growth and mold fat production by using nutritional supplements for enhancing the production of mold fat.

In tap water was prepared a cultivation medium with a composition per liter of water as follows: 25 g dried *Saccharomyces cerevisiae* yeast mass; 20 g dextrose monohydrate; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The employed baker's yeast consisted of fresh yeast (Fresh yeast, Finnish Yeast Ltd., Finland), which had been over-dried overnight (50-80° C.). The cultivation medium was sterilized at a temperature of 121° C. for 15 min. The mold cultivations were conducted in 250 ml Erlenmeyer flasks in a 50 ml cultivation liquid volume.

The employed *Mortierella isabellina* and *Mucor circinelloides* mold inoculants were spore suspensions stored for 2 days at a temperature of 4° C., which had been prepared by supplementing the germinating PDA Petri dish mold culture with 12 ml sterile water and by releasing the spores within the water by means of an inoculation loop. Each mold was subjected on a yeast medium to parallel 50 ml cultivations, which were inoculated with 500 µl of the above-mentioned spore suspension. The mold cultures were incubated at a temperature of 28° C. in a shaker with a mixing rate of 160 rpm.

The mold cultures were supplemented, during cultivation, after 1 day of incubation, first in a 50 ml cultivation medium volume, with 2 ml of a 500 g/l glucose solution, after 2 days of incubation, in a 52 ml volume, with 2 ml of a 500 g/l glucose solution, and after 4 days of incubation, in a 44 ml cultivation medium volume, with 4 ml of a 455 g/l glucose solution.

Dry matter content samples picked up from the mold cultures were filtered, washed with distilled water, and dried for about 1 day at a temperature of about 50-70° C. Fatty acid analysis samples picked up from the *M. isabellina* cultures were deep frozen as such and cold dried prior to a fatty acid analysis. The fat content assessments of *M. circinelloides* mold were conducted from a mold material that had been filtered, washed, and dried in a heating cabinet, and ground thereafter in a mortar.

It was concluded that the *M. isabellina* mold had produced significant amounts of mold biomass over 4 days of incubation, the mold mass having a dry matter content of 14 g/l. With continued incubation, the dry matter content increased to 32 g/l over 7 days of incubation. At this point, the fat content of dry mold matter was 40% of the dry matter. Respectively, the *M. circinelloides* mold produced 8.1 g/l dry matter over 4 days of incubation. As the incubation was continued to 8 days, the dry mold matter content increased to 10 g/l, the dry matter having a fat content of 34%.

Based on the results, fat-free yeast cell mass can be used for the production of mold mass and the actual fat production can be implemented with other nutritional supplements.

5. Dried and Ground *Saccharomyces cerevisiae* Yeast Mass Supplemented with Salts The object was to demonstrate that yeasts, which do not inherently accumulate fat, can function as contributors to mold growth and mold fat production more effectively when yeast cells have been broken prior to use as opposed to cells used in an intact condition.

In tap water was prepared a cultivation medium with a composition per liter of water as follows: 25 g dried and ground *Saccharomyces cerevisiae* yeast mass; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The employed baker's yeast consisted of fresh yeast (Fresh yeast, Finnish Yeast Ltd., Finland), which had been oven-dried overnight (50-80° C.) and ground thereafter in a mortar. The cultivation medium was sterilized at a temperature of 121° C. for 15 min. The mold cultivations were conducted in 250 ml Erlenmeyer flasks in a 50 ml cultivation medium volume.

The employed *Mortierella isabellina*, *Mucor circinelloides* and *Trichoderma reesei* mold inoculants were spore suspensions, which were prepared by adding 12 ml sterile water into germinating PDA Petri dish cultures of the above-mentioned molds and by releasing the spores within the water by means of an inoculation loop. 500 µl of *M. isabellina* and *M. circinelloides* molds were inoculated into 50 ml cultivation media. In addition to this, two cultivation media were inoculated with both *M. isabellina* and *T. reesei* spore suspensions, both 500 µl, for a mixed culture in a single cultivation medium. The mold cultures were incubated at a temperature of 28° C. in a shaker with a mixing rate of 160 rpm. Samples picked up from the mold cultures were filtered, washed with distilled water, and dried for about 1 day at a temperature of about 60-70° C.

The *M. circinelloides* mold produced 4.7 g/l of dry matter over 8 days of incubation. Respectively, the *M. isabellina* mold produced 3.9 g/l of dry matter over 7 days of incubation, and the mixed culture of *M. isabellina* and *T. reesei* molds produced 3.6 g/l over 8 days of incubation.

In light of the results, the grinding of residual cell mass enables promoting the usefulness of cell mass and the yield of mold biomass from residual cell mass.

6. Dried and Ground *Saccharomyces cerevisiae* Yeast Mass Supplemented with Salts and Glucose The objective was to demonstrate that low fat yeasts promote mold growth and fat production better in the use of broken cells by using nutritional supplements for enhancing fat production.

In tap water was prepared a cultivation medium with a composition per liter of water as follows: 25 g dried and ground *Saccharomyces cerevisiae* yeast mass; 20 g dextrose monohydrate; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The next cultivation medium was prepared in tap water, followed by sterilizing the cultivation medium at a temperature of 121° C. for 15 min. The employed baker's yeast consisted of fresh yeast (Fresh yeast, Finnish Yeast Ltd., Finland), which had been oven-dried overnight (50-80° C.). The mold cultivations were conducted in 250 ml Erlenmeyer flasks in a 50 ml cultivation medium volume.

The employed *Mortierella isabellina* and *Mucor circinelloides* mold inoculants were spore suspensions stored for 2 days at a temperature of 4° C., which had been prepared by supplementing the germinating PDA Petri dish culture of mold with 12 ml sterile water and by releasing the spores within the water by means of an inoculation loop. Each mold was subjected on a yeast medium to parallel 50 ml cultivations, which were inoculated with 500 µl of the above-mentioned spore suspension. The mold cultures were incubated at a temperature of 28° C. in a shaker with a mixing rate of 160 rpm.

The mold cultures were supplemented with a glucose solution during cultivation by adding first, 1 day after the incubation, 2 ml of 500 g/l glucose solution to a 50 ml cultivation medium volume, 2 days after the incubation 2 ml of 500 g/l glucose solution to a 52 ml volume, and 4 days after the incubation 4 ml of 455 g/l glucose solution to a 44 ml cultivation medium volume.

Dry matter content samples picked up from the mold cultures during cultivation were filtered, washed with distilled water, and dried for about 1 day at a temperature of about 50-70° C. Fatty acid analysis samples picked up from *M. isabellina* cultures were deep frozen as such and cold-dried prior to a fatty acid analysis. The fat content assessments of *M. circinelloides* mold were conducted on mold material which had been filtered, washed, and dried in a heating cabinet and ground thereafter in a mortar.

*M. isabellina* mold grew to a dry matter content of 16 g/l over 4 days of incubation. With continued incubation, the dry matter content increased and was 32 g/l after 7 days, at which point the mold mass had a fat content which was 35% of the dry matter. Respectively, *M. circinelloides* mold grew to a dry matter content of 5.1 g/l over 4 days of incubation. With continued incubation, the dry matter content increased to 6.9 g/l, at which point the mode mass had a fat content which was 18% of the dry matter.

Based on the results, a cultivation medium suitable for the growth of mold can be supplemented with other nutrient components for the production of fat.

Example 9

Heterotrophically cultivated *Brachiomonas submarina* algal whole cells were used as a cultivation medium for the molds *Mortierella isabellina* and *Mucor circinelloides*.

The glucose-cultivated *Brachiomonas submarina* algal biomass, with 42% of its dry matter being fat, was used to prepare a 20 g/l dry algal mass-containing cultivation medium in tap water. The cultivation medium had its pH adjusted with NaOH to the value 5.7. The cultivation medium was sterilized by autoclaving at 120° C. for 15 min. The cultivations were conducted in 250 ml Erlenmeyer flasks with a cultivation medium of 50 ml in volume.

From the *Mortierella isabellina* and *Mucor circinelloides* molds were prepared spore suspensions. In order to prepare a spore suspension, the germinating PDA Petri dish culture of each mold was supplemented with 9 ml sterile water, in which the spores were released by means of an angle wand. Each mold was subjected on an algal medium to parallel 50 ml cultivations, which were inoculated with 500 µl of the above-mentioned spore suspension. The mold cultures were incubated at a temperature of 28° C. in a shaker with a mixing rate of 160 rpm. Samples picked up from the cultivations were filtered and washed with distilled water. The filtration was followed by drying the samples overnight at a temperature of about 70° C.

After 5 days of incubation, it was concluded, by microscoping with a phase contrast microscope at a magnification of 100-1000 times, that *M. isabellina* mold grows weakly on *Brachiomonas* algal mass. On the other hand, *M. circinelloides* mold grew well on the algal mass on the basis of microscoping.

After 5 days, the *M. circinelloides* mold had a dry matter content of about 10 g/l (variation 6-14 g/l) and a fat content of about 47%. As opposed to that, the *M. isabellina* mold had not grown significantly over the course of 11 days on *Brachiomonas* algal mass alone.

The results indicate that algal whole cells can be utilized as a nutrient for the cultivation of mold and the production of mold-based fat. The results further indicate that the ability of mold to make use of algal whole cells is a species-related feature of mold.

Example 10

1. Unbroken *Chlorella pyrenoidosa* Algal Mass as a Cultivation Medium

Heterotrophically cultivated *Chlorella pyrenoidosa* algal whole cells were used as a cultivation medium for the molds *Mortierella isabellina* and *Mucor circinelloides*.

From glucose-cultivated *Chlorella pyrenoidosa* algal biomass, with 10% of its dry matter being fat, was prepared a cultivation medium containing 20 g dry algal mass per liter of tap water. The cultivation medium had its pH adjusted with 2 M NaOH solution to the value 6.0. The cultivation liquid was sterilized by autoclaving at 121° C. for 15 min. the mold cultivations were conducted in 250 ml Erlenmeyer flasks with a cultivation medium 50 ml in volume.

From *Mortierella isabellina*, *Mucor circinelloides* and *Trichoderma reesei* molds were prepared spore suspensions. In order to prepare a spore suspension, the germinating PDA Petri dish culture of each mold was supplemented with 12 ml sterile water, within which the spores were released by means of an inoculation loop. *M. isabellina* and *M. circinelloides* were subjected on an algal medium to parallel 50 ml cultivations, which were inoculated with 500 µl of the above-mentioned spore suspension. In addition, on an algal medium were conducted parallel 50 ml cultivations by using a mixed culture of *M. isabellina* and *T. reesei* molds, in which case the cultivation medium was supplemented with 500 µl of the spore suspension of both these molds. The mold cultures were incubated for the period of 7 days at a temperature of 28° C. in a shaker with a mixing rate of 160 rpm. Samples picked up from the cultivations were filtered and washed with distilled water. The filtration was followed by drying the samples overnight at a temperature of 60° C.

In the *M. isabellina* mold culture, the content of dry mold matter after 7 days of incubation was 3.1 g/l, the mold mass having at this point a fat content of 15%. Hence, there was 0.5 g/l fat in the cultivation medium. Thus, the *Chlorella* algal mass worked as a nutrient for *M. isabellina* mold distinctly better than the *Brachiomonas* algal mass described in example 7, which the mold was not able to consume to any significant extent. *M. circinelloides* mold used *Chlorella* algal mass for growth more effectively than *M. isabellina* mold and the dry mold matter content of *M. circinelloides*, when using *Chlorella* algal mass as a nutrient, was 7.6 g/l after 7 days. *M. circinelloides* mold was also more effective in terms of using *Chlorella* mass for fat production and the fat content of dry mold matter was 21%. The amount of fat in the cultivation medium was 1.6 g/l. The most effective transformation of *Chlorella* algal mass into mold mass occurred in the mixed culture of *M. isabellina* and *T. reesei* molds, in which the content of dry mold matter was respectively 9.2 g/l. The mold masses had a total fat content of 8.3%, the cultivation medium having a mold fat content of 0.8 g/l.

The results indicate that algal masses of various algal species are applicable in whole and also in low fat versions as a nutrient for the cultivation of mold and the production of mold-based fat. The results further indicate that the ability of mold to make use of algal whole cells depends not only on a mold species but also on an algal species, and that, in order to maximize the production and growth of fat, it is important to find a suitable mold-algae combination.

According to the methods section, the hydrolyzed, untreated *Chlorella pyrenoidosa* algal mass contained hydrolyzable sugars a maximum of about 30% of the dry weight of algal mass. When comparing the resulting yield of mold fat to the amount of hydrolyzable sugars, it was possible to conclude that the molds had produced fat from the sugars of algal mass with a yield of 27% in the case of *M. circinelloides* mold and with yields of 8-13% in the case of *M. isabellina* as well as in the mixed culture of *M. isabellina* and *T. reesei* molds. The use of a mixed culture increased the yield in the case of *M. isabellina* mold.

2. Unbroken *Chlorella* Algal Mass Supplemented with Minerals

Heterotrophically cultivated *Chlorella* pyrenoidosa algal whole cells were used as a cultivation medium for the molds *Mortierella isabellina* and *Mucor circinelloides*.

From glucose-cultivated cold-dried *Chlorella pyrenoidosa* algal biomass, which contained 10% fat of its dry matter, was prepared a cultivation medium in tap water with a composition per liter of water as follows: 22.7 g cold-dried *Chlorella pyrenoidosa algal mass*; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The cultivation medium was sterilized by autoclaving at 121° C. for 15 min. The mold cultivations were conducted in 250 ml Erlenmeyer flasks with a cultivation medium of 50 ml in volume.

From *Mortierella isabellina*, *Mucor circinelloides* and *Trichoderma reesei* molds were prepared spore suspensions. In order to prepare a spore suspension, the germinating PDA Petri dish culture of each mold was supplemented with 12 ml sterile water, within which the spores were released by means of an inoculation loop. *M. isabellina* and *M. circinelloides* molds were subjected on an algal medium to parallel 50 ml cultivations, which were inoculated with 500 μl of the above-mentioned spore suspension. On an algal medium were further conducted parallel 50 ml cultivations by using a mixed culture of *M. isabellina* and *T. reesei* molds, in which case the cultivation medium was supplemented with 500 μl of the spore suspension of these particularly molds. The mold cultures were incubated at a temperature of 28° C. in a shaker with a mixing rate of 160 rpm. Samples picked up from the cultivations were filtered and washed with distilled water. The filtration was followed by frying the sample overnight at a temperature higher than 60° C.

In the *M. isabellina* mold culture, the content of dry mold matter was 8.6 g/l after 7 days of incubation, the mold mass having at this point a fat content of 9.1%. A supplementation of *Chlorella* mold mass with minerals promoted the growth of mold. A respective growth enhancement was observed neither in the *M. circinelloides* culture nor in the mixed culture of *M. isabellina* and *T. reesei* molds, and after 7 days of incubation the respective dry mold matter contents were 5.9 g/l and 8.3 g/l. The respective fat contents of dry mold matters were 10.5% and 5.9%.

The results indicate that the supplementation of algal mass used as a cultivation medium promotes the growth of molds, depending on a mold species.

Example 11

Fat-producing *Mortierella isabellina* and *Mucor circinelloides* molds were cultivated with household biowaste for producing mold fat.

A cultivation medium was prepared from biowaste with a composition as follows: 418 g raw potatoes, 35 g peeled raw carrot, 105 g potato peels, 41 g carrot peels, 147 g dry rice, 70 g banana peels, 87 g orange peels, 17 g hand tissues, 60 g French bread crust, 89 g coffee grounds and a filter bag. The presented amounts were wet weights unless indicated otherwise. The biowaste was supplemented with 1.2 liters of water, followed by cooking the waste material for about 40 minutes. The cooking was followed by adding to the mass 0.5 liter of water, after which it was homogenized by using an OBH Nordica Juice Bar blender. The thus produced mass was supplemented with 0.5 liter of water per 0.6 liter of mass, after which the biomass was diluted into a mold cultivation medium by adding 200 ml water per 300 ml biowaste. The biowaste media were sterilized by autoclaving at 121° C. for 20 min. The thereby prepared biowaste cultivation medium had a dry matter content of 57 g/l.

From *M. isabellina* and *M. circinelloides* molds were prepared spore suspensions to serve as inoculants. In order to prepare a spore suspension, the germinating PDA Petri dish culture of each mold was supplemented with 12 ml sterile water, within which the spores were suspended.

The mold cultivations were conducted in 250 Erlenmeyer flasks in a cultivation medium volume of 50 ml. Each mold was subjected to parallel 50 ml cultivations, which were inoculated with 500 μl of the above-mentioned spore suspension. The cultivations were conducted at a temperature of 28° C. with a shaking speed of 160 rpm.

From the mold cultures were extracted samples which were deep frozen and cold-dried as such. The cold-dried samples were subjected to the assessment of fat content according to a method described in the methods section.

On the basis of fat content results, it was concluded that the molds had produced major amounts of fat in the biowaste medium. The fat content of dry matter in the untreated biowaste medium was determined to be 2.8% of dry matter, the cultivation medium having a fat content of 1.6 g/l. When the biowaste material had been used as a cultivation medium for *M. circinelloides* mold, the fat content of total dry matter in the biowaste medium and household biomass had increased to 12.8% after 7 days of incubation, whereby the fat content in the cultivation medium was 6.4 g/l. The *M. isabellina* mold produced fat on household biowaste even more effectively than the *M. circinelloides* mold and, after 7 days of incubation, the fat content of total dry matter in the biowaste medium and household biomass was 16.6%. Respectively, at this point, the fat content in the cultivation medium was 8.7 g/l.

The results indicate that starch- and cellulose-containing biowaste is suitable as such for a cultivation medium and a carbon source in the production of mold fat for various fat-producing mold species.

Example 12

The molds *Mortierella isabellina* and *Mucor circinelloides* were cultivated by using xylose as a carbon source for the production of fat.

In tap water was prepared a cultivation medium, which per liter contained 10 g yeast extract, 20 g peptone, and 40 g xylose. The cultivation medium was either sterilized as such by autoclaving at 120° C. for 15 min or from the cultivation medium components were prepared separate concentrates which were sterilized as presented above and added into the aseptically sterilized water for providing a composition as set forth in the table. The cultivations were conducted in 250 ml Erlenmeyer flasks with a cultivation medium of 50 ml in volume.

From *M. isabellina* and *M. circinelloides* molds were prepared spore suspensions. In order to prepare a spore suspension, the germinating PDA Petri dish culture of each mold was supplemented with 9 ml sterile water, within which the spores were released by means of an angle wand. Each mold was subjected to parallel 50 ml cultivations, which were inoculated with 500 μl of the above-mentioned spore suspension.

From the mold cultivations were extracted samples, which were filtered and washed with about 250 ml of distilled water. The filtration was followed by drying the samples at a temperature of 70-95° C. The samples were assessed for dry matter and fat contents as described in the methods section.

In a first test series, the parallel *M. isabellina* mold cultures were incubated at a temperature of 28° C. in a shaker with a mixing rate of 160 rpm, first for the duration of 7 days, after which the mixing rate was increased to 250 rpm for the next 6 days. In the test series, the *M. isabellina* cultures of 50 ml in volume were each supplemented with 2 g of xylose after 6 days of incubation. With this test arrangement, the *M. isabellina* mold did not produce pellets and appeared in short loose hyphae. On a xylose medium, the mold produced 40% fat of dry matter over the course of 13 days of incubation.

In a second test series, the *M. isabellina* cultures were incubated throughout the entire cultivation process at a temperature of 28° C. with a shaking speed of 160 rpm. In the test series, the parallel *M. isabellina* cultures of 50 ml in volume were supplemented with 1 g of xylose after 3 days of incubation, and another 1 g of xylose was added after 4 days of incubation into the cultures which were 40 ml in volume after sample extractions.

After the first 4 days of incubation, the *M. isabellina* mold had produced about 15 g/l dry matter, of which 4.1% was fat. With continued incubation in both test series, in one of the parallel cultivation flasks the mold created pellets consisting of long hyphae, and in the other of the parallel cultivation flasks, the mold cells grew in short hyphae loose from each other. Depending on the mode of growing, the *M. isabellina* mold grew, after 8 days of incubation, to a dry matter content of 22-35 g/l. In pellet form, the mold had a weaker growth. With the latter test arrangement, the fat content of dry *M. isabellina* mold mass increased to 5% in mold mass grown in the form of pellets and to 24% in the one developed in short and loose mode of growth.

The *M. circinelloides* mold was incubated at a temperature of 28° C. for the first 7 days at a mixing rate of 160 rpm, and thereafter at a shaking speed of 250 rpm for the next 5 days. Parallel *M. circinelloides* cultures of 50 ml in volume were supplemented with xylose in the amount of 1 g after 1 day of incubation and another 2 g after 6 days of incubation. The fat content of *M. circinelloides* mold increased, with xylose as a carbon source, to 20 g/l over the course of 12 days of incubation.

Based on the results, it could be concluded that both five- and six-carbon monosaccharides worked as growth substrates for molds and as energy sources for the production of fat.

Example 13

As a sole carbon source, the media contained either yeast extract in small amounts or a mixture of the equivalent amount of yeast extract and cellulose. In tap water was prepared a yeast extract medium to serve as a control medium. The medium had a composition per liter of water as follows: 1.0 g/l yeast extract; 1.0 g $(NH_4)_2SO_4$; 1.0 g $MgSO_4.7\,H_2O$; 0.7 g $K_2HPO_4.3\,H_2O$; 1.0 g $KH_2PO_4$; 0.2 g $CaCl_2.2H_2O$. In tap water was further prepared a medium, which contained not only the above-mentioned components but also 40 g pine cellulose per liter of water. The media were sterilized by autoclaving at 121° C. for 15 min. The cultivations were conducted in 250 ml Erlenmeyer flasks with a cultivation medium of 50 ml in volume. These medias were tested as cultivation and fat production media for *Mortierella isabellina* mold and for a mixed culture of *M. isabellina* and *Trichoderma reesei* molds.

Control cultivations were used for finding out the ability of molds to produce fat solely on a yeast extract medium, which was the foundation of a cellulose medium. Respectively, under examination was also the ability of molds to produce fat independently on a cellulose medium.

A spore suspension was prepared to serve as an inoculant for control cultivations. An *M. isabellina* MPA Petri dish culture was supplemented with 9 ml of YPD liquid. The mold cultivation medium MPA or malt extract peptone agar had a per-liter-composition of 30 g malt extract, 3 g bactopeptone, and 15 g Agar No. 1. Spores were released from the Petri dish by means of an inoculation loop within the YPD liquid. Thus prepared spore suspension was inoculated in the amount of 300 µl into parallel 50 ml yeast extract medium controls and into parallel 50 ml cellulose media. Incubation was applied to the cultures with 160 rpm shaking at a temperature of 26° C.

On the basis of microscoping (lens magnification 10-100×, phases 1-4), it was concluded that the *M. isabellina* mold had germinated on a yeast extract control medium during 1 day of incubation. Respectively, on the basis of microscoping, it was found that the *M. isabellina* mold had germinated over 7 days of incubation on a cellulose medium, but the cell showed no signs of fat globules developing as an indication of inceptive fat production. Mold had not grown any better on a cellulose medium as compared to a yeast extract medium control. On the basis of microscoping, the cells had not developed fat globules even after 17 days of incubation, i.e. the production of fat had not begun. It was judged that mold had become germinated by the use yeast extract and, after this, had no longer been able to grow by the use of cellulose.

In view of enhancing the fat production of *M. isabellina* mold with cellulose as a carbon source, the examination was directed to the cultivation of *M. isabellina* mold as a mixed culture with *T. reesei* mold of known hydrolytic capacity.

From *Trichoderma reesei* and *Mortierella isabellina* PDA Petri dish cultures were prepared spore suspensions. The cultures were supplemented with 12 ml sterile water, the spores were released by means of an inoculation loop, and liquids, which contained the spores, were transferred into sterile vessels. 500 µl of the *T. reesei* spore suspension, held still for 4 days at a temperature of 4° C., and 1000 µl of the *M. isabellina* spore suspension, held still for 5 days at a temperature of 4° C., were inoculated for a mixed culture into parallel 50 ml cellulose media. The cultures were incubated at a temperature of 28° C. with mixing at 160 rpm. 4 ml samples picked up from the cultures were centrifuged at a speed of 6000 rpm for 10 minutes, after which the supernatant was removed and the samples were washed with 5 ml of distilled water. The samples were re-washed as described and deep frozen. The deep frozen samples were cold-dried prior to a fatty acid assessment.

Microscoping after 1 day of incubation revealed an abundant amount of spores, which probably were non-germinated *M. isabellina* spores. The *T. reesei* mold had started growing in small amounts. The *M. isabellina* mold was yet to germinate after 2 days of incubation.

In cellulose medium cultures, inoculated with *M. isabellina* and *T. reesei* molds, it was found on the basis of microscoping, after 22 days of incubation, that the *M. isabellina* mold had produced fat in the cells. The assessment was made on the basis of fat globules formed on mold hyphae. On the basis of a fatty acid analysis, the mold was found having produced fat, and the dry matter, which contained biomasses of both molds and residual cellulose, had a fat content of 1.8-4.8%. The amount of fat in the cultivation medium was 0.5-1.5 g/l.

Based on the tests, it can be concluded that the ability of mold to use cellulose for growth and/or fat production is an organism-specific capability. It can be further concluded that the known hydrolytic capacity of *T. reesei* mold promotes the ability of other molds to grow and produce fat.

Example 14

In tap water was prepared a cultivation medium, in which the carbon source consisted of starch and a small amount of yeast extract. The medium had a per-liter-composition as follows: 40 g starch (corn-based starch from Merck); 1.0 g yeast extract; 1.0 g $(NH_4)_2SO_4$; 1.0 g $MgSO_4.7H_2O$; 0.7 g $K_2HPO_4.3H_2O$; 1.0 g $KH_2PO_4$; 0.2 g $CaCl_2.2H_2O$. The medium was sterilized by autoclaving at 121° CC for 15 min.

The mold cultivations were conducted in 250 ml Erlenmeyer flasks with a medium of 50 ml in volume. Inoculated into parallel 50 ml starch media were 300 µl of *M. isabellina* spore suspension. The suspension had been prepared by slurring the spores from the MPA culture of *M. isabellina* mold with 9 ml of YPD liquid. The inoculated starch liquids were incubated in 160 rpm shaking at a temperature of 26° C. first for 2 days and this was followed by raising the cultivation temperature to 28° C. Dry matter content and fatty acid samples picked up from the starch medium cultures were centrifuged at a rotating speed of 6000 rpm for 10 minutes, after which the supernatant was removed. The samples were washed twice with 5 ml of water and the supernatant was removed as above between the washing cycles. The samples were deep frozen and cold-dried prior to analyses.

The *M. isabellina* mold grew on a starch medium during 8 days of incubation to a dry matter content of 17 g/l, at which point the mold mass had a fat content of 28%.

Example 15

In tap water were prepared cultivation media, which contained per liter either 120 g *Nannochloropsis* algae or 120 g *Rhodosporidium* yeast mass. Preparation of the algal medium was conducted by using autotrophically cultivated algae (e.g. *Nannochloropsis*), which had been spray-dried. The yeast medium was prepared from *Rhodosporidium toruloides* yeast mass, which had been extruded and leached after extrusion. After the yeast mass had been slurried, the medium was homogenized with an Ultra Turrax device (at low speeds of rotation). The cultivation media were sterilized by autoclaving at 121° C. for 15 min.

The *Mucor circinelloides* mold inoculants was prepared by releasing the mold spores from a PDA Petri dish culture by means of an angle wand into 12 ml of sterile water. Thus prepared spore suspension was inoculated in the amount of 500 µl into parallel 50 ml algal medium and yeast medium batches. The inoculated cultivation liquids were incubated at a temperature of 28° C. in a shaker with a shaking speed of 160 rpm.

On the basis of microscoping, the mold germinated in both medias during 1 day of incubation. The *M. circinelloides* mold mass was extracted by filtration from the algae cells and cultivation liquid of the algal medium after 7 days of incubation and, respectively, after 8 days of incubation from the cultivation liquid and yeast cells of the yeast medium. The filtered mold mass was washed with water for the removal of algal and yeast residues, after which the mold mass was dried first to a temperature of 95° C. for 2-4 h, and thereafter to a temperature of 70° C. for the duration of 3 days.

The algal permeate obtained in extractions was centrifuged at a speed of 6000 rpm for 15 minutes, followed by the extraction of supernatant. The algal mass concentrated this way from permeate, and the supernatant were subjected to further processes to find out whether the mold treatment of algal mass promotes the hydrolyzation of algal mass by chemical treatments. The yeast permeate was not concentrated and further assessments were conducted directly therefrom.

From the germinating PDA Petri dish culture of *Trichoderma reesei* mold was prepared a spore suspension the same way as from the *M. circinelloides* mold culture. The *T. reesei* spore suspension was inoculated in the amount of 500 µl into parallel 50 ml algal medium and yeast medium batches and the cultures were incubated the same way as the *M. circinelloides* cultures.

Over 3 days of incubation, the *T. reesei* mold had grown both in yeast and algal media. The *T. reesei* mold masses were extracted after 10 days of incubation by filtering from algal and yeast cells, and the mold masses were washed for the removal of algal and yeast cell residues with 250 ml of distilled water. The mold masses and both yeast and algal cultivation medium permeates were dried at a temperature of 95° C. for the duration of 1 day. Prior to chemical hydrolysis treatments, the permeates were stored at a temperature of 4° C.

The mold masses were treated chemically and the sugars were analyzed as described in the methods section.

The untreated *Rhodosporidium* yeast mass, which was used as a cultivation medium for molds, contained hydrolysable sugars per dry matter, prior to mold treatments, a total of 25.4% of the dry matter. As for the dry matter of yeast mass, 20.4% consisted at this point of glucose and 5.0% of galactose.

The untreated *Nannochloropsis* algal mass, which was used as a cultivation medium for molds, contained hydrolysable sugars per dry matter, prior to mold treatments, a total of 10%. As for the dry matter of algal mass, 4.8% was glucose, 1.1% was xylose, 3.3% was galactose, and 0.8% was mannose.

When using *Rhodosporidium* yeast as a cultivation medium, the *M. circinelloides* mold produced 14 g/l dry mold matter over 8 days of incubation. The hydrolysis results indicated that the *M. circinelloides* mold mass, which had been cultivated with *Rhodosporidium* yeast, included per dry matter a total of 24% of hydrolysable sugars. Calculated per dry mold matter, 20% of the sugars consisted of glucose, 3% was mannose, and 1% was galactose.

After the *M. circinelloides* mold had grown on a *Rhodosporidium*-yeast containing medium, the yeast permeate, which was left over after the extraction of mold from the cultivation medium, enabled hydrolyzing a total of 14.5% of sugars per dry matter of the permeate. As for hydrolysable sugars per yeast permeate dry matter, glucose made up 2.1%, galactose 7.7%, and mannose 4.8%.

When the cultivation medium comprised *Nannochloropsis* algae, the *M. circinelloides* mold produced dry matter 38 g/l over 7 days of incubation. In hydrolysis, the thus produced *M. circinelloides* mold mass yielded a total of 26% hydrolysable sugars per dry matter. Calculated per dry mold matter, the sugars contained 24% of glucose, 1% of mannose, and the amount of galactose fell short of 1%. After the *M. circinelloides* mold had grown on a *Nannochloropsis*-algae containing medium, the algal permeate, which was left over after the extraction of mold from the cultivation medium, only yielded 0-0.6% of glucose per dry matter. Other sugars were not observed.

On a *Rhodosporidium*-yeast containing medium, the *T. reesei* mold produced 21 g/l of dry matter over 10 days of incubation. As a result of hydrolysis, the thus cultivated *T. reesei* mold mass produced 6.1% of glucose, 7% of mannose, and 4.3% of galactose, i.e. a total of 20.4% of hydrolysable sugars per dry matter.

After the *T. reesei* mold had grown on a *Rhodosporidium*-yeast containing medium, the yeast permeate, which was left over after the extraction of mold from the cultivation medium, enabled hydrolyzing therefrom a total of 13% of sugars per dry matter of the permeate. As for hydrolysable sugars per yeast permeate dry matter, glucose made up 0-1.8%, galactose 5.7-7.9%, and mannose 5.2-5.6%.

On a *Nannochloropsis*-algae comprising medium, the *T. reesei* mold produced dry matter in the amount of 21 g/l over 10 days of incubation. On the basis of hydrolysis results, the thus cultivated *T. reesei* mold mass contained glucose 4.3%, mannose 0.9%, and galactose 2.1%, i.e. the total amount of hydrolysable sugars in mold mass per dry matter was 7.1%.

After the *T. reesei* mold had grown on a cultivation medium consisting of *Nannochloropsis*-algae, the algal permeate, which was left over after the extraction of mold from the cultivation medium, enabled hydrolyzing therefrom a total of 12.1% of sugars per dry matter of the permeate. As for hydrolysable sugars, 11% of dry permeate weight consisted of glucose. The respective value for mannose was 1.1% and galactose was not found at all.

All in all, a conclusion can thus be made that the residual cell mass of a known single-cell fat production process, the residual cell mass of autotrophically cultivated algae, and the residual cell mass of heterotrophically cultivated algae constitute a beneficial cultivation and fat production medium component for mold, from which can be further released fermentation-capable sugar for the production of single-cell mass and single-cell fat.

Example 16

It was demonstrated that the residual cell mass, resulting from a known yeast-based single-cell fat production process after the extraction of fat, is suitable for mold as a nutrient, as well as for the cultivation of mold and the production of mold fat when hydrolyzed chemically and supplemented with nutrients.

A cultivation medium, in which the carbon source consisted of yeast hydrolyzate and a small amount of yeast extract, was prepared in a yeast hydrolyzate solution diluted to a 50% solution in tap water. The medium had a per-liter-composition as follows: 1.0 g yeast extract; 1.0 g $MgSO_4.7H_2O$; 0.7 g $K_2HPO_4.3H_2O$; 1.0 g $KH_2PO_4$; 0.2 g $CaCl_2.2H_2O$. The yeast hydrolyzate had been prepared by applying a hydrolysis described in the methods section to hydrolyze *Lipomyces starkeyi* yeast mass, which had developed in the production process of a known single-cell fat and from which fats had been extracted. The thus obtained hydrolyzate was neutralized prior use and it contained hydrolysis-evolved sugars 70 g/l. The medium was sterilized at 121° C. for 15 min.

The effect on two molds was examined. Therefore, parallel cultivation medium flasks were inoculated with 500 µl of *Mortierella isabellina* spore suspension and, respectively, parallel cultivation medium flasks with 500 µl of *Mucor circinelloides* spore suspension. The spore suspensions, used as mold inoculants, had been prepared by suspending the spores of a PDA Petri-dish cultivated, germinating mold culture in 12 ml of sterile water. The mold cultivations were conducted in a 50 ml cultivation medium volume in 250 ml Erlenmeyer flasks. The cultures were incubated at a temperature of 28° C. in a shaker with a mixing rate of 160 rpm. During cultivation, the *M. isabellina* cultures were supplemented with 10 ml of the above-described yeast hydrolyzate after 11 days of incubation. Respectively, the *M. circinelloides* cultures were supplemented with 20 ml of yeast hydrolyzate after 6 days of incubation.

Samples picked up from *M. isabellina* mold cultivations for dry matter and fat content assessments were filtered through a Whatman 3 filter for the extraction of mold mass, and were washed with distilled water. The samples were dried at a temperature of 60° C. and ground prior to a fatty acid analysis. As for samples picked up from *M. circinelloides* mold cultures, the mold mass was extracted therefrom by centrifugation and washed with distilled water. The *M. circinelloides* samples were cold-dried prior to a fatty acid analysis. The samples' fat contents were determined as described in the methods section.

The *M. circinelloides* mold produced on a hydrolyzate medium, over 18 days of incubation, 24 g/l of dry matter, of which 9% was fat. Respectively, the *M. isabellina* mold produced 21 g/l of dry matter. Of the *M. isabellina* dry mold matter, 28% was fat.

Based on the test, a conclusion can be made that the residual cell masses, resulting from yeasts used in known single-cell fat production processes, are applicable, when chemically hydrolyzed, for the cultivation of mold and the production of mold-based fat.

The yeast hydrolyzate was also found to promote the growth of molds, as the molds produced significant amounts of biomass even though the employed nutritional supplements were just 1 g/l yeast extract and no other nitrogen sources.

LITERATURE

Meng, X., Yang, J., Xu, X., Zhang, L., Nie, Q. and Xian M., Biodiesel production from oleaginous microorganisms, *Renew. Energ.* 34 (2009) 1-5.

Ratledge, C. and Hopkins, S. Lipids from microbial sources. In *Modifying Lipids for Use in Food*, edit. F. Gunstone, Woodhead Publishing, Cambridge 2006, pp. 80-113.

Ratledge C, Seekstra H, Cohen Z, Fichtali J. 2005. Downstream processing, extraction, and purification of single cell oils. In *Single Cell Oils*, edit. Z. Cohen, C Ratledge C, AOCS Press, Champaign, Ill., U.S, pp. 202-219.

Ratledge C. and Wilkinson S., *Microbial lipids* Volume 1, Academic Press, London 1988, p. 963.

Ratledge C. and Wilkinson S., *Microbial lipids* Volume 2, Academic Press, London 1989, p. 726.

Suutari, M., Liukkonen, K. and Laakso, S., Temperature adaptation in yeasts: the role of fatty acids, *J. Gen. Microbiol.* 136 (1990) 1469-1474

The invention claimed is:

1. A method for production of fat, characterized in that the method comprises the steps of:
   (a) contacting a mold capable of fat production in a cultivation medium with
      a residual mass separated, after a fat recovery or in connection with the fat recovery, from a single-cell mass obtained from a single-cell oil production process wherein the single-cell oil production process is a yeast-based or algae-based single-cell oil production process and the residual mass comprises the residue of yeast or algae cells treated for the fat recovery, and allowing the mold to produce fat; and
   (b) recovering resulting fat or passing the mold mass to a single-cell oil production process.

2. The method according to claim 1, characterized in that the method is integrated as part of a single-cell oil production process.

3. The method according to claim 1, wherein the fat recovery process in step (b) is the same as in the single-cell oil production process of step (a).

4. The method according to claim 1, characterized in that the method functions separately of the single-cell oil production process.

5. The method according to claim 1, characterized in that the cultivation medium of the mold capable of fat production is supplemented with nutrients.

6. The method according to claim 1, characterized in that the cultivation medium of the mold capable of fat production is supplemented with natural or human activity-based fractions, which contain hydrocarbons.

7. The method according to claim 1, characterized in that the mold capable of producing fat is capable of producing enzymes disrupting cell structures or hydrolyzing ingredients of cell structures.

* * * * *